US011954862B2

(12) United States Patent
Ren et al.

(10) Patent No.: US 11,954,862 B2
(45) Date of Patent: Apr. 9, 2024

(54) JOINT ESTIMATION OF HEART RATE AND RESPIRATORY RATE USING NEURAL NETWORKS

(71) Applicant: NVIDIA Corporation, Santa Clara, CA (US)

(72) Inventors: Yuzhuo Ren, Sunnyvale, CA (US); Niranjan Avadhanam, Saratoga, CA (US); Rajath Bellipady Shetty, Sunnyvale, CA (US)

(73) Assignee: NVIDIA Corporation, Santa Clara, CA (US)

( * ) Notice: Subject to any disclaimer, the term of this patent is extended or adjusted under 35 U.S.C. 154(b) by 344 days.

(21) Appl. No.: 17/479,648

(22) Filed: Sep. 20, 2021

(65) Prior Publication Data

US 2023/0091371 A1 Mar. 23, 2023

(51) Int. Cl.
*G06T 7/10* (2017.01)
*A61B 5/024* (2006.01)
(Continued)

(52) U.S. Cl.
CPC ............. *G06T 7/10* (2017.01); *A61B 5/024* (2013.01); *A61B 5/087* (2013.01); *G16H 30/40* (2018.01);
(Continued)

(58) Field of Classification Search
CPC ............ G06T 7/10; G06T 2207/20081; G06T 2207/20084; G06T 2207/30088;
(Continued)

(56) References Cited

U.S. PATENT DOCUMENTS

| 2014/0323822 | A1* | 10/2014 | Addison | A61B 5/0295 600/301 |
| 2022/0130015 | A1* | 4/2022 | Yun | G06T 3/4046 |
| 2022/0222466 | A1* | 7/2022 | Hassani | G06V 10/82 |

FOREIGN PATENT DOCUMENTS

WO WO 2021/061699 * 4/2021

OTHER PUBLICATIONS

Chen et al., "DeepPhys: Video-Based Physiological Measurement Using Convolutional Attention Networks", Proceedings of the European Conference on Computer Vision (ECCV), 2018, pp. 349-365 (Year: 2018).*

(Continued)

*Primary Examiner* — Qian Yang
(74) *Attorney, Agent, or Firm* — Leydig, Voit & Mayer, Ltd.

(57) ABSTRACT

A neural network system leverages dual attention, specifically both spatial attention and channel attention, to jointly estimate heart rate and respiratory rate of a subject by processing images of the subject. A motion neural network receives images of the subject and estimates heart and breath rates of the subject using both spatial and channel domain attention masks to focus processing on particular feature data. An appearance neural network computes a spatial attention mask from the images of the subject and may indicate that features associated with the subject's face (as opposed to the subject's hair or shoulders) to accurately estimate the heart and/or breath rate. Channel-wise domain attention is learned during training and recalibrates channel-wise feature responses to select the most informative features for processing. The channel attention mask is learned during training and can be used for different subjects during deployment.

22 Claims, 13 Drawing Sheets

Process a sequence of images of a subject by layers of a motion neural network model to produce channels of feature vectors in two spatial dimensions
155

Apply a learned channel attention mask to the channels of the feature vectors to generate at least one of an estimated heart rate or an estimated breath rate for the subject
160

(51) Int. Cl.
*A61B 5/087* (2006.01)
*G16H 30/40* (2018.01)
(52) U.S. Cl.
CPC ............... *G06T 2207/20081* (2013.01); *G06T 2207/20084* (2013.01); *G06T 2207/30088* (2013.01); *G06T 2207/30201* (2013.01)
(58) Field of Classification Search
CPC ......... G06T 2207/30201; G06T 7/0016; G06T 7/11; G06T 7/194; A61B 5/024; A61B 5/087; A61B 5/0077; A61B 5/0816; A61B 5/7267; G16H 30/40; G16H 40/67; G16H 50/20; G16H 50/70
See application file for complete search history.

(56) References Cited

OTHER PUBLICATIONS

Wu, H.Y., et al., "Eulerian video magnification for revealing subtle changes in the world," ACM transactions on graphics (TOG), vol. 3, No. 4, pp. 1-8, 2012.

Balakrishnan, G., et al., "Detecting pulse from head motions on video," in Proceedings of the IEEE Conference on Computer Vision and Pattern Recognition, 2013, pp. 3430-3437.

Bartula, M., et al., "Camera-based system for contactless monitoring of respiration," in 2013 35th Annual International Conference of the IEEE Engineering in Medicine and Biology Society (EMBC). IEEE, 2013, pp. 2672-2675.

Chen, W., et al., "Deepphys: Video-based physiological measurement using convolutional attention networks," in Proceedings of the European Conference on Computer Vision (ECCV), 2018, pp. 349-365.

Janssen, R., et al., "Video-based respiration monitoring with automatic region of interest detection," Physiological measurement, vol. 37, No. 1, p. 100, 2015.

Wang, W., et al., "A novel algorithm for remote photoplethysmography: Spatial subspace rotation," IEEE transactions on biomedical engineering, vol. 63, No. 9, pp. 1974-1984, 2015.

Liu, X., et al., "Multi-task temporal shift attention networks for on-device contactless vitals measurement," arXiv preprint arXiv:2006.03790, 2020.

Wang, W., et al., "Algorithmic principles of remote ppg," IEEE Transactions on Biomedical Engineering, vol. 64, No. 7, pp. 1479-1491, 2016.

Tasli, H.E., et al., "Remote ppg based vital sign measurement using adaptive facial regions," in 2014 IEEE international conference on image processing (ICIP), IEEE, 2014, pp. 1410-1414.

Wang, W., et al., "Robust heart rate from fitness videos," Physiological measurement, vol. 38, No. 6, p. 1023, 2017.

Lewandowska, M., et al., "Measuring pulse rate with a webcam—a non-contact method for evaluating cardiac activity," in 2011 federated conference on computer science information systems (FedCSIS). IEEE, 2011, pp. 405-410.

Haan, G.D., et al., "Robust pulse rate from chrominance-based rppg," IEEE Transactions on Biomedical Engineering, vol. 60, No. 10, pp. 2878-2886, 2013.

Wang, W., et al., "Discriminative signatures for remote-ppg," IEEE Transactions on Biomedical Engineering, vol. 67, No. 5, pp. 1462-1473, 2019.

Wang, W., et al., "Modified rgb cameras for infrared remote-ppg," IEEE Transactions on Biomedical Engineering, vol. 67, No. 10, pp. 2893-2904, 2020.

Lin, J., et al., "TSM: Temporal shift module for efficient video understanding," 2019 IEEE, in CVF International Conference on Computer Vision (ICCV), 2019, pp. 7082-7092.

Niu, X., et al., "Rhythmnet: End-to-end heart rate estimation from face via spatial-temporal representation," IEEE Transaction on Image Processing, vol. 29, pp. 2409-2423, 2019.

Rapczynski, P., et al., "Effects of video encoding on camera-based heart rate estimation," IEEE Transactions on Biomedical Engineering, vol. 66, No. 12, pp. 3360-3370, 2019.

Yu, Z., et al., "Remote heart rate measurement from highly compressed facial videos: an end-to-end deep learning solution with video enhancement," in Proceedings of the IEEE/CVF International Conference on Computer Vision, 2019, pp. 151-160.

Li, C., et al., "Skeleton-based gesture recognition using several fully connected layers with path signature features and temporal transformer module," in Proceedings of the AAAI Conference on Artificial Intelligence, vol. 33, No. 01, 2019, pp. 8585-8593.

Wu, K.H., et al., "Action recognition using multi-scale temporal shift module and temporal feature difference extraction based on 2d cnn," Journal of Software Engineering and Applications, vol. 14, No. 5, pp. 172-188, 2021.

Jaderberg, M., et al., "Spatial transformer networks," arXiv preprint arXiv:1506.02025, 2015.

Hu, J., et al., "Squeeze-and-excitation networks," in Proceedings of the IEEE conference on computer vision and pattern recognition, 2018, pp. 7132-7141.

Fu, J., et al., "Dual attention network for scene segmentation," in Proceedings of the IEEE/CVF Conference on Computer Vision and Pattern Recognition, 2019, pp. 3146-3154.

Long, J., et al., "Fully convolutional networks for semantic segmentation," in Proceedings of the IEEE Conference on Computer Vision and Pattern Recognition, 2015, pp. 3431-3440.

Wang, Q., et al., "ECA-Net: Efficient channel attention for deep convolutional neural networks," 2020 IEEE, in CVF Conference on Computer Vision and Pattern Recognition (CVPR).

Heusch, G., et al., "A reproducible study on remote heart rate measurement," arXiv preprint arXiv:1709.00962, 2017.

\* cited by examiner

JOINT ESTIMATION OF HEART RATE AND RESPIRATORY RATE USING NEURAL NETWORKS

BACKGROUND

Heart rate and respiratory rate measurement is a vital step for diagnosing many diseases and conditions. Non-contact camera based physiological measurement tend to be more accessible and convenient in Telehealth compared with contact instruments such as fingertip oximeters because non-contact methods reduce risk of infection. However, remote physiological signal measurement is challenging due to environment illumination variations, head motion, facial expression, etc. There is a need for addressing these issues and/or other issues associated with the prior art.

SUMMARY

Embodiments of the present disclosure relate to techniques for improved joint heart rate and breath rate estimation. Systems and methods are disclosed that provide a neural network system for estimating both heart rate and respiratory (e.g., breath) rate with higher accuracy, and reduced system complexity and latency compared with conventional systems. The neural network system leverages dual attention, specifically both spatial attention and channel attention, to jointly estimate heart rate and respiratory rate of a subject by processing a video of the subject.

According to embodiments, a detection network sequences of images of the subject and timestamps of the images. Bounding boxes and subject features or landmarks (e.g., facial features) are generated using the detection network for the subject. From the bounding boxes of contiguous or near-contiguous frames, a motion map is generated that encodes a movement of features between frames. From the sequence of images, an appearance map, which encodes an appearance (e.g., as an average of color values of a pixel location) of a subject, and a skin segmentation mask that includes a binary semantic mask of regions within the images that depict a subject's skin are generated. Using the appearance map and the skin segmentation mask, an appearance neural network computes a spatial attention mask from the images of the subject that may indicate features associated with the subject's face (as opposed to the subject's hair or shoulders) for precise estimation of the positions of pixels corresponding to features of the subject's face. A motion neural network uses the motion map and the sequence of images to estimate a heart rate and a respiratory rate of the subject in the images. The spatial attention masks are provided to a motion network to direct a focus of the motion neural network, thereby producing results with higher accuracy, better precision, and greater efficiency than otherwise possible with conventional systems. In contrast to conventional systems, such as those described above, accuracy of the estimations are improved by applying an attention mechanism in both spatial domain and channel-wise domain. Spatial domain attention enhances spatial encoding which locates facial regions that contain a strong physiological signal response. Channel-wise domain attention recalibrates channel-wise feature responses to select the most informative features. The channel attention mask is learned during training and may be used for different subjects during deployment.

In an embodiment, the neural network system learns to estimate the heart and breath rates based on a correlation between the two rates. In an embodiment, accuracy of the neural network system is improved when the spatial attention is based on a skin segmentation mask that identifies a region that includes the facial skin (forehead, cheek, and nose), neck, and chest to provide additional data (e.g., blood circulation) for estimating the heart and breath rates.

A method, computer readable medium, and system are disclosed for jointly estimating at least one of a heart rate or breath rate of a subject. In an embodiment, a sequence of images of the subject is processed by layers of a motion neural network model to produce channels of feature vectors in two spatial dimensions and a learned channel attention mask is applied to the channels of the feature vectors to jointly generate at least one of an estimated heart rate or an estimated breath rate for the subject.

BRIEF DESCRIPTION OF THE DRAWINGS

The present systems and methods for joint heart rate and breath rate estimation are described in detail below with reference to the attached drawing figures, wherein.

DETAILED DESCRIPTION

Figure 1A:
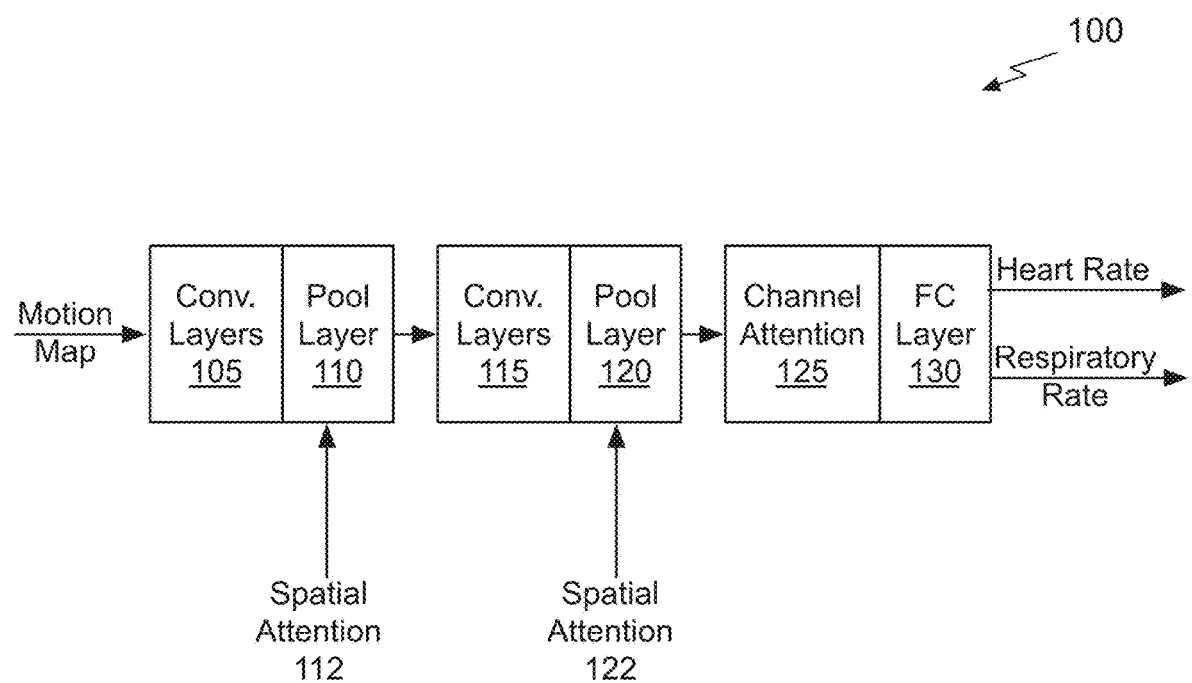
FIG. 1A illustrates a block diagram of an example joint heart rate and breath rate estimation network system suitable for use in implementing some embodiments of the present disclosure.

Systems and methods are disclosed related for joint heart rate and breath rate estimation network. There are many use cases for heart and/or breath rate estimation, particularly in automotive, healthcare, and gaming environments. In an automotive environment, heart rate and breath rate estimation may be used to monitor an operator's stress, fatigue, or incapacitation. Based on the estimates, minimum risk maneuvers may be initiated (e.g., change music, modify braking settings, pull over, emergency call, etc.) Heart rate and breath rate estimation may also be used to perform child presence detection. In a gaming environment, heart rate and breath rate estimation may be used to measure a user's level of engagement and/or excitement. In a healthcare environment, heart rate and breath rate estimation may be used for telemedicine or touchless on-site screening.

Non-contact camera-based physiological measurement is an active research field and draws significant attention especially during pandemics and the increasing popularity of remote medical attention. Non-contact camera-based physiological measurement reduces infection risks and enables telehealth and remote health monitoring. The underlying principle for camera-based physiological measurement is capturing subtle skin color changes or subtle motions caused by blood circulation and respiratory motion. The skin color changes and motions correspond to changes in light reflection. Imaging techniques can be used to measure volumetric changes of blood in the surface of the skin by capturing subtle skin color and motion changes due to blood flow, and during respiration.

Imaging Photoplethysmography (iPPG) and remote Photoplethysmography (rPPG) technologies are based on the measurement of subtle changes in light reflected from the skin. Image Ballistocardiogram (iBCG) technology is based on the measurement of mechanical force of blood pumping around the body which causes subtle motions. Both heart rate and respiratory rate can be recovered using iPPG, rPPG, and/or iBCG based methods. Camera-based heart rate and respiratory rate estimation is challenging because the skin color change and motions caused by blood circulation may be so subtle that it's easily corrupted by environment illumination variations, head motion, facial expression, etc.

For the theoretical optical principle of the model, Shafer's dichromatic reflection model (DRM) may be used to model lighting reflection and physiological signals. An RGB color (red, green, blue) value of the $k^{th}$ skin pixel in an image can be defined by a time-varying function:

$$C_k(t) = I(t) \cdot v_s(t) + v_d(t) + v_n(t)$$

$$I(t) = I_0 \cdot (1 + \Psi(m(t), \Theta(b(t), r(t))))$$

$$v_s(t) = (u_s \cdot (s_0 + \Phi(m(t), \Theta(b(t), r(t)))))$$

$$v_d(t) = (u_d \cdot d_0 + u_p \cdot (\Theta(b(t), r(t)))) \quad \text{Eq. (1)}$$

where $C_k(t)$ denotes a vector of the RGB values; $I(t)$ is the illuminance intensity; $v_s(t)$ and $v_d(t)$ are specular and diffusion reflection respectively; $v_n(t)$ denotes camera sensor's quantization noise. $I(t)$, $v_s(t)$ and $v_d(t)$ can all be decomposed into stationary part $I_0$, $u_s \cdot s_0$, $u_d \cdot d_0$ and time-varying part ($I_0 \cdot \Psi(\bullet)$, $u_s \cdot \Phi(\bullet)$, $u_p \cdot \Theta(\bullet)$) where $m(t)$ denotes all non-physiological variations such as illumination variations from light source, head motion and facial expressions; $\Theta(b(t), r(t))$ denotes time-varying physiological signal which is a combination of both pulse $b(t)$ and respiration $r(t)$ information; $\Psi(\bullet)$ denotes the intensity variation observed by camera; $\Phi(\bullet)$ denotes the varying parts of the specular reflections; $u_s$ and $u_d$ denotes the unit color vector of the light source and skin-tissue respectively; $u_p$ denotes the relative pulsatile strengths. $I_0$ denotes stationary part of illuminance intensity; $s_0$ and $d_0$ denotes the stationary specular and diffusion reflection respectively.

The skin reflection model in Eq. (1) demonstrates that the relation between RGB value of $k^{th}$ skin pixel $C_k(t)$ and physiological signal $\Theta(b(t), r(t))$ is non-linear and the non-linearity complexity can be caused by non-stationary terms, such as illuminance variation, head motion, facial expression, camera intensity variation, etc. A machine learning model is desired to model the complex relationship between $C_k(t)$ and $\Theta(b(t), r(t))$.

FIG. 1A illustrates a block diagram of an example joint heart rate and breath rate estimation network system 100 suitable for use in implementing some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the joint heart rate and breath rate estimation network system 100 is within the scope and spirit of embodiments of the present disclosure.

In an embodiment, the joint heart rate and breath rate estimation network system 100 comprises a motion neural network that receives spatial attention 112, spatial attention 122, and a motion map and estimates heart and breath rates of the subject using both spatial and channel domain attention masks to focus processing on particular feature data. In one or more embodiments, the motion map may be computed as per-pixel differences between two images in a sequence (e.g., video frames) of a subject. The images may be acquired by a camera including, but not limited to RGB (red, green, blue), IR (infrared), and RGB_IR cameras. In an embodiment, RGB images may be interleaved with IR images. In an embodiment, the interleaving may be determined by a signal to noise ratio (SNR) of the images or outside environment, i.e., IR images is robust under low illumination condition (e.g., during night) and illumination changes (e.g., passing shadow during driving). IR images can be used to cancel illumination changes in RGB images. In another embodiment, RGB images and IR image may be concatenated together to form four channel (red, green, blue, infrared) input to the network to improve the network robustness compared to RGB only or IR image only network.

In an embodiment, the motion map is computed as per-pixel differences for a region of interest comprising the subject's face within each of the two images in the sequence. In an embodiment, a separate neural network or processing unit identifies the region of interest as a bounding box surrounding the subject's face. The spatial attentions 112 and 122 may be encoded as masks, are appearance-based, and may be generated by an attention neural network for each image. In an embodiment, the images are compressed as needed based on available network bandwidth or storage resources. The compression level may be variable (i.e., depending on the available bandwidth) or fixed. To improve robustness and generality of the joint heart rate and breath rate estimation network system 100, during training the input images may be compressed (or not) at varying levels (e.g., compression ratios).

Each processing layer of the motion neural network applies learned parameters to an input to produce feature data in spatial dimensions height (H) and width (W) for multiple channels (C). The feature data within a single channel is a feature vector. In an embodiment the convolutional layers 105 comprises two layers, that are each N×32×72×72 (N×C×H×W) and the input images are 1×3×72×72. N is a number of frames (e.g., images) which also equals the number of consecutive motion maps. When N>1, the motion neural network may learn temporal information from an adjacent frame's motion map, improving robustness. In an embodiment, a temporal shift operation is applied to the input of one or more of the layers in convolutional layers 105 before the input is convolved with the learned parameters to provide an input to a pooling layer 110. Temporal shifting may reduce complexity of 3D convolution, by shifting a portion of the channels along the temporal dimension to facilitate information exchange among images that are nearby in terms of time.

The pooling layer 110 reduces the dimension of feature maps. The pooling layer 110 receives the element-wise multiplication between the convolution layer 105 and the spatial attention 112. In an embodiment the pooling layer 110 is N×36×36×36. Because physiological signals are not uniformly distributed on human skin, the spatial attention 112 (e.g., soft spatial attention mask) may define higher weights in regions where physiological signals are stronger to improve network accuracy. For example, a spatial attention mask that is computed from the images of the subject may indicate features associated with the subject's face (as opposed to the subject's hair or shoulders) to more accurately estimate the heart and/or breath rate. In other words, the spatial attentions 112 and 122 define spatial relationships between the features at a particular layer.

The output of the pooling layer 110 is processed by convolutional layers 115 before being input to a pooling layer 120 that also receives spatial attention 122. In an embodiment, a temporal shift operation is applied to the input of one or more of the layers in convolutional layers 115 before the input is convolved with the learned parameters to provide an input to the pooling layer 120. The pooling layer 120 receives element-wise multiplication between the convolution layer 115 and the spatial attention 122. In an embodiment, the pooling layer 120 may be implemented with dimensions of size N×64×18×18. In an embodiment, the spatial attention 112 is after a second convolution layer and the spatial attention 122 is after a fourth convolution layer. The spatial attention 112 and 122 provide improved face skin localization and define much lower weights for the background region compared with relevant regions of the subject's face.

An output of the pooling layer 120 is input to a channel attention layer 125. Channel-wise domain attention is learned during training and recalibrates channel-wise feature responses to select the most informative features for processing. In an embodiment, one-dimensional convolution is performed followed by a Sigmoid function to learn channel attention. The channel attention mask may be implemented with dimensions of size 1×1×c, providing a per-channel mask, meaning that each channel c will be assigned a weight which is learned during training. In contrast with spatial attention that selects discriminative features in the H and W dimensions, channel-wise attention selects discriminative features in the channel dimension. The channels with higher weights have more informative features, while channels with lower weights are less important for estimating the heart and/or breath rate. The learned channel attention mask that is applied to each feature vector by the channel attention layer 125 may be generalized, and therefore can be used for subjects during deployment that were not available during training. In other words, the same learned channel attention mask generalizes well to estimate the heart and/or respiratory rate for subjects not seen during training. In an embodiment, subject-specific channel attention masks and spatial attention mask may be learned and selected for use during deployment.

After channel attention is applied, an output of the channel attention layer 125 is input to a fully-connected (FC) layer 130 that generates an estimated heart rate and/or respiratory rate. Inserting the channel attention layer 125 before the final average pooling performed by FC layer 130, causes the motion neural network to emphasize informative features and suppress less useful ones.

In an embodiment, the motion neural network computes Blood Volume Pulse (BVP) for heart rate estimation and/or respiratory wave for respiratory rate estimation. In an embodiment, the motion neural network operates in a multitask manner, computing both the BVP and respiratory wave. In an embodiment, the estimated heart rate and respiratory rate are represented as a pulse waveform sequence and respiratory waveform sequence, respectively. To extract the heart rate and respiratory rate in beats per minute, a Butterworth bandpass filter may be applied to the output of the FC layer 130. In an embodiment, filter cut-off frequencies of 0.67 and 4 Hz are used for heart rate, and 0.08 and 0.50 Hz are used for respiratory rate. The filtered signals may be divided into 10-second windows, and a Fourier transform may be applied to produce dominant frequencies as the heart rate and respiratory rate.

More illustrative information will now be set forth regarding various optional architectures and features with which the foregoing framework may be implemented, per the desires of the user. It should be strongly noted that the following information is set forth for illustrative purposes and should not be construed as limiting in any manner. Any of the following features may be optionally incorporated with or without the exclusion of other features described.

Figure 1B:
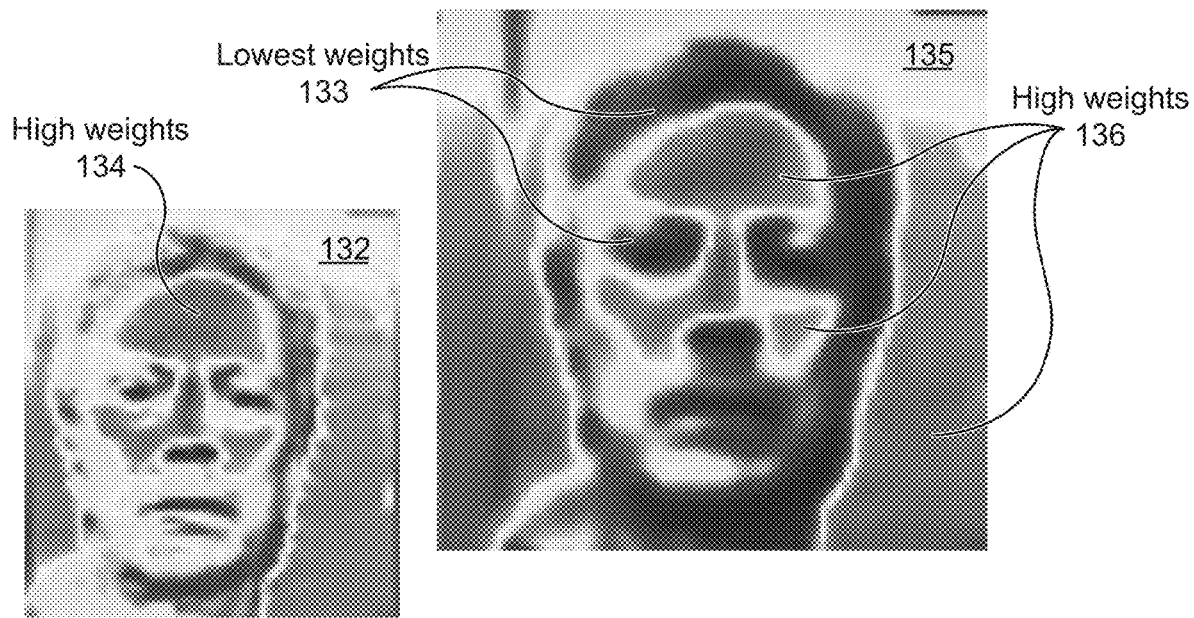
FIG. 1B illustrates spatial attention maps suitable for use in implementing some embodiments of the present disclosure.
Figure 1B:
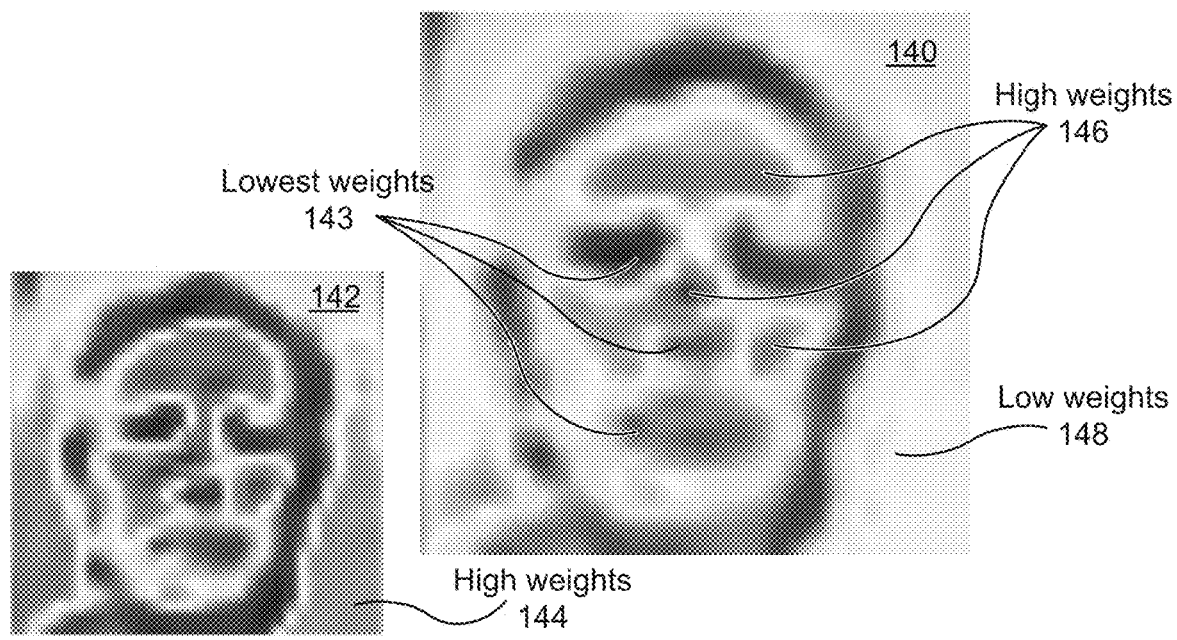

FIG. 1B illustrates spatial attention maps 135 and 140 suitable for use in implementing some embodiments of the present disclosure. In an embodiment, the spatial attentions 112 and 122 comprise the spatial attention maps 142 and 140, respectively. In an embodiment, the spatial attention maps 142 and 140 are generated by an appearance neural network, as described in conjunction with FIG. 2A.

Comparing the spatial attention map 135 with spatial attention map 132 that is generated using a conventional technique without channel attention, the spatial attention map 132 shows high weights 134 for the subject's cheeks, nose, and forehead. However, the boundary of the high weight region in the spatial attention map 132 is blurry and shows false positive high weights in the subject's eyelid region. Also, values of the high weights 134 in the spatial attention map 132 are less than values of high weights 136 in the spatial attention map 135 for the subject's cheeks, nose, and forehead. Similarly, lowest weights 133 for the subject's eyes, hair, lips, chin, and neck in the spatial attention map 135 are much more clearly defined and have lower values compared with the same regions in the spatial attention map 132. Overall, the spatial attention map 135 clearly shows larger contrast between the face region and background and better boundary localization on the skin region where physiological signal is stronger (forehead and cheeks) compared with the spatial attention map 132.

Comparing spatial attention map 142, which is generated using the conventional technique with channel attention and that corresponds with the spatial attention map 140, the spatial attention map 140 shows larger contrast between face region and background with better boundary localization which indicates a better spatial and channel-wise feature extraction. In particular, the background region of the spatial attention map 142 has high weights 144 whereas, the same region of the spatial attention map 140 has low weights 148, correctly indicating that the background region is less important. Similar to the spatial attention map 135, the spatial attention map 140 defines lowest weights 143 for the subject's eyes, nostrils, and lips while maintaining high weights 146 for the subject's forehead, nose, and cheeks. In summary, compared with the spatial attention maps 132 and 142, the spatial attention maps 135 and 140 have higher weights on skin with better localization and have lower weights on background regions, which improves robustness of the motion neural network and reduces background noise.

Figure 1C:
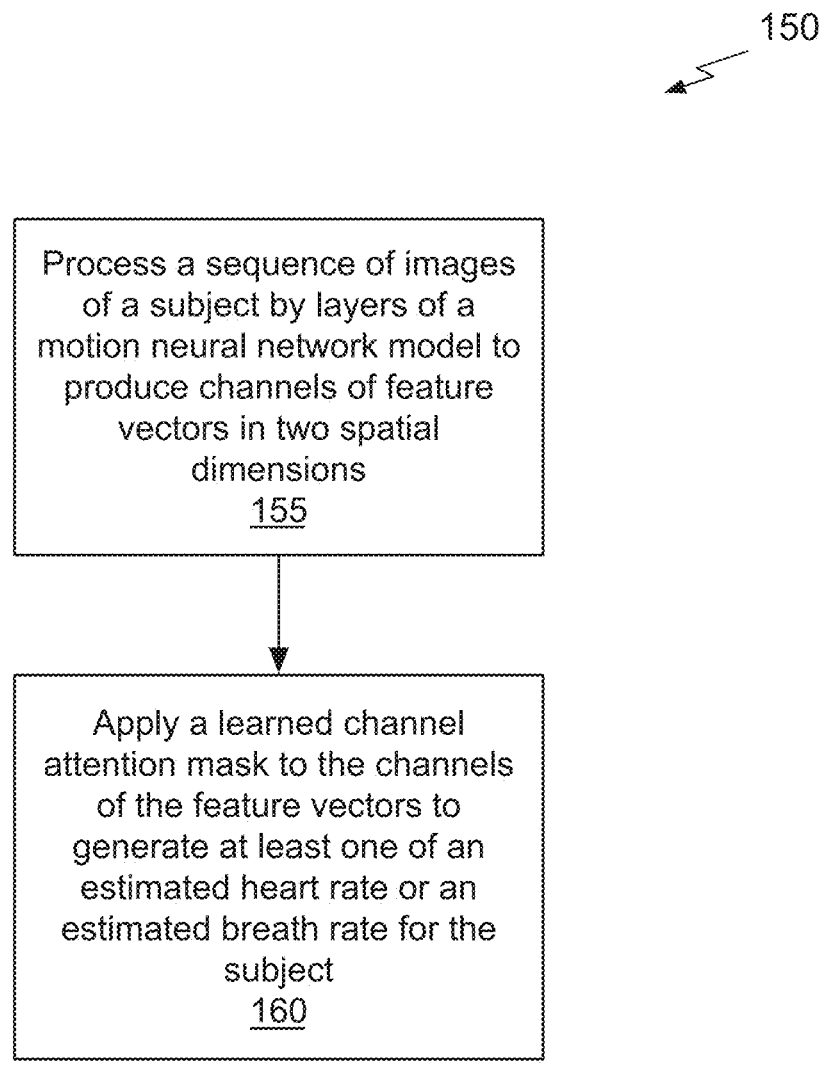
FIG. 1C illustrates a flowchart of a method for joint heart rate and breath rate estimation, in accordance with an embodiment.

FIG. 1C illustrates a flowchart of a method 150 for joint heart rate and breath rate estimation, in accordance with an embodiment. Each block of method 150, described herein, comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a standalone application, a service or hosted service (standalone or in combination with another hosted service), or a plug-in to another product, to name a few. In addition, method 150 is described, by way of example, with respect to the system 100 of FIG. 1A. However, this method may additionally or alternatively be executed by any one system, or any combination of systems, including, but not limited to, those described herein. Furthermore, persons of ordinary skill in the art will understand that any system that performs method 150 is within the scope and spirit of embodiments of the present disclosure.

At step 155, a sequence of images of a subject is processed by layers of a motion neural network model to produce channels of feature vectors in two spatial dimensions. In an embodiment, the motion neural network model comprises the joint heart rate and breath rate estimation network system 100. In an embodiment, the processing comprises applying at least one spatial attention mask between the layers. In an embodiment, the at least one appearance channel attention mask is applied between a convolution layer and a pooling layer.

In an embodiment, a frame rate at which each image in the sequence of images is received is variable and the processing comprises adjusting at least one of the estimated heart rate or the estimated breath rate based on the frame rate. In an embodiment, the joint heart rate and breath rate estimation network system 100 receives a timestamp with each image that may be used to compute the frame rate. In an embodiment, one or more images in the sequence of images are compressed. In an embodiment, the one or more images are compressed at varying levels.

In an embodiment, for each image in the sequence, an appearance map and a skin segmentation mask are processed by an attention neural network to compute the at least one spatial attention mask. In an embodiment, the attention neural network applies at least one appearance channel attention mask between layers of the attention neural network to compute the at least one spatial attention mask. In an embodiment, the appearance map comprises a portion of each image of the subject that includes a face, neck, and chest region of the subject. In an embodiment, the skin segmentation mask comprises a mask separately identifying facial skin including a forehead, cheeks, nose, neck and chest regions in each image of the subject from background, hair, eyes, eyebrows, and beard regions in each image of the subject.

At step 160, a learned channel attention mask is applied to the channels of the feature vectors to generate at least one of an estimated heart rate or an estimated breath rate for the subject. In an embodiment, the learned channel attention mask is a per-channel mask, meaning that each channel will be assigned a weight which is learned during training, the channels with higher weights have more informative features, while channels with lower weights are less important for estimating the heart and/or breath rate. In an embodiment, the learned channel attention mask is applied to each feature vector between the pooling layer 120 and the final fully-connected layer 130.

In an embodiment, at least one of the steps of processing and applying are performed on a server or in a data center and the sequence of images is streamed to the server or the data center from a user device. In an embodiment, at least one of the steps of processing and applying are performed on a server or in a data center and the at least one of an estimated heart rate or an estimated breath rate is streamed to a user device. In an embodiment, at least one of the steps of processing and applying are performed within a cloud computing environment. In an embodiment, at least one of the steps of processing and applying are performed for training, testing, or certifying a neural network employed in a machine, robot, or autonomous vehicle. In an embodiment, at least one of the steps of processing and applying is performed on a virtual machine comprising a portion of a graphics processing unit.

Figure 2A:
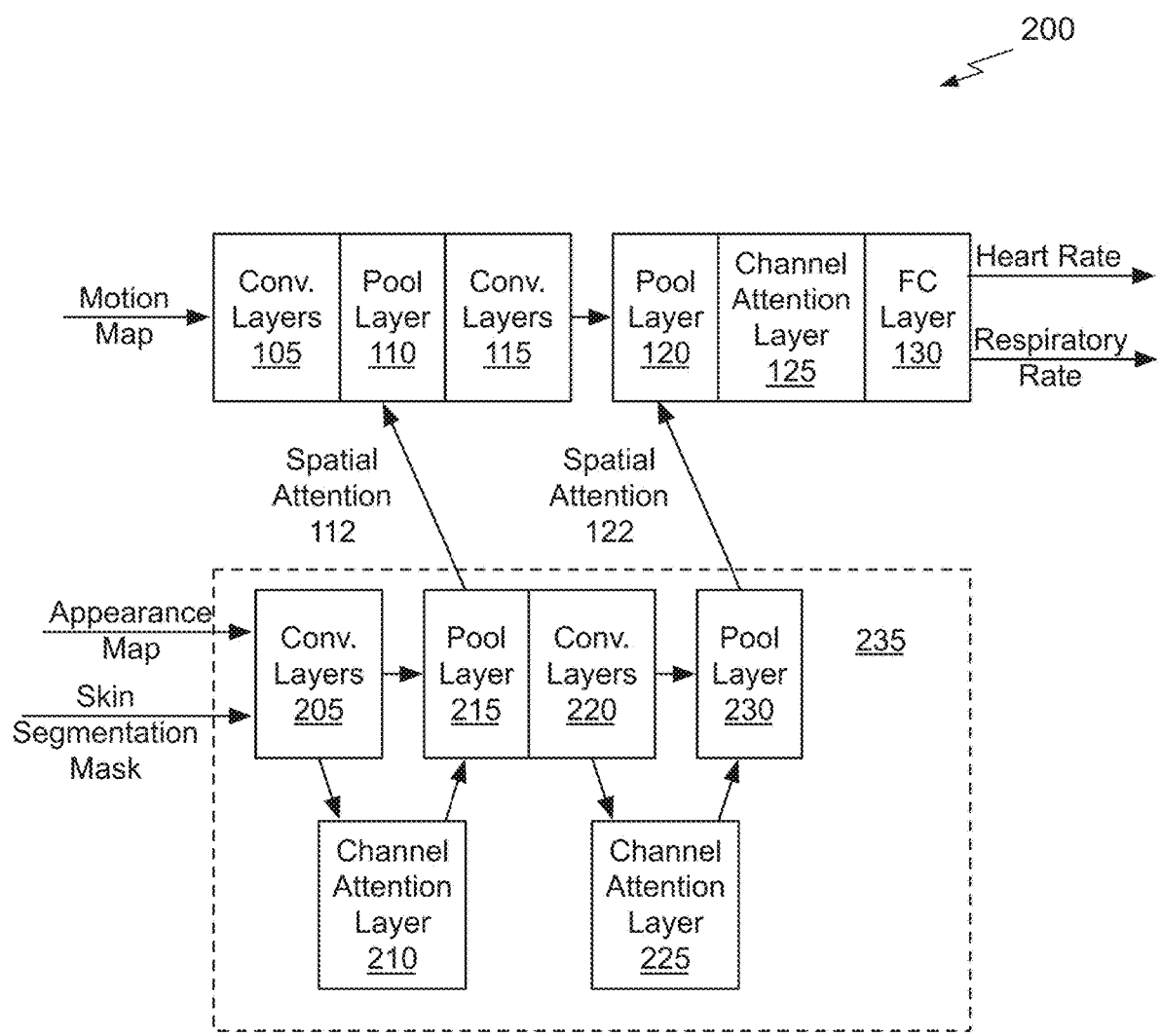
FIG. 2A illustrates a block diagram of another example joint heart rate and breath rate estimation network system suitable for use in implementing some embodiments of the present disclosure.

FIG. 2A illustrates a block diagram of another example joint heart rate and breath rate estimation network system 200 suitable for use in implementing some embodiments of the present disclosure. The joint heart rate and breath rate estimation network system 200 comprises the motion neural network shown in FIG. 1A in addition to an appearance neural network 235.

It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the joint heart rate and breath rate estimation network system 200 is within the scope and spirit of embodiments of the present disclosure.

The appearance neural network 235 receives an appearance map and a skin segmentation mask as inputs and applies learned parameters to compute spatial attentions 112 and 122 for each image frame. In an embodiment, the appearance map (e.g., RGB image) is a cropped portion of a captured image of the subject. In an embodiment, the captured image is cropped to a bounding box identifying a face region (may include upper part of neck or chest) of the subject. In an embodiment, a task-specific neural network (not shown) is used to identify the bounding box.

In an embodiment, a task-specific neural network (not shown) is used to identify facial landmarks from which the skin segmentation binary mask is derived. In an embodiment, the skin segmentation mask (e.g., binary segmentation) that is a mask identifying facial skin, such as forehead, cheeks regions, nose, neck and chest regions of the subject. In an embodiment, the skin segmentation mask is a binary map with "skin" pixels labeled as "1" (True) and background pixels, hair pixels, pixels on eyes, eyebrows, beard, etc. labeled as "0" (False).

The attention neural network 235 computes the spatial attentions 112 and 122 using the appearance map, skin segmentation mask, and learned channel attention masks that are applied by channel attention layers 210 and 225. Through training, the attention neural network 235 learns which region(s) in the appearance map are more important to estimate heart rate or breath rate. When the spatial attention weights are examined, higher weights are found in the forehead and cheek regions. The purpose of the skin segmentation mask is to inform the attention neural network 235 that higher weights should be used in the skin region where the heart rate/breath rate signal can be detected, further improving accuracy of the estimations.

In an embodiment, the appearance neural network 235 generates spatial attentions 112 and 122 for input to pooling layers 110 and 120, respectively, using a 1×1 convolution filter. Then the spatial attentions 112 and 122 are multiplied with feature maps in the motion neural network via element-wise multiplication. In an embodiment, the masked feature map $\mathbb{Z}^k$, where k is the layer index, that is passed to pooling layers 110 and 120 is calculated as $$\mathbb{Z}^k = \frac{H_k W_k \cdot \sigma(\omega^k \mathbb{X}_a^k + b^k)}{2\|\sigma(\omega^k \mathbb{X}_a^k + b^k)\|_1} \odot \mathbb{X}_m^k \qquad \text{Eq. (2)}$$

where σ(•) is sigmoid activation function, $\omega^k$ is the 1×1 convolution kernel, $b^k$ is the bias, $\mathbb{X}_m^k$ is the motion neural network feature map, $\mathbb{X}_a^k$ is the appearance neural network 235 feature map, ⊙ is element-wise multiplication, $H_k$ and $W_k$ are height and width of the feature map.

Like the motion neural network that includes the channel attention layer 125, the appearance neural network 235 includes channel-wise attention layers, specifically the channel attention layers 210 and 225. The channel attention layers 210 and 225 are between convolutional layers 205 and pooling layer 215 and between convolutional layers 220 and pooling layer 230, respectively. By inserting channel-wise attention layer(s) in the appearance neural network 235, better facial spatial attention masks can be generated. Inserting channel attention layers 210 and 225 helps the appearance neural network 235 emphasize informative features and suppress less useful ones.

Figure 2B:
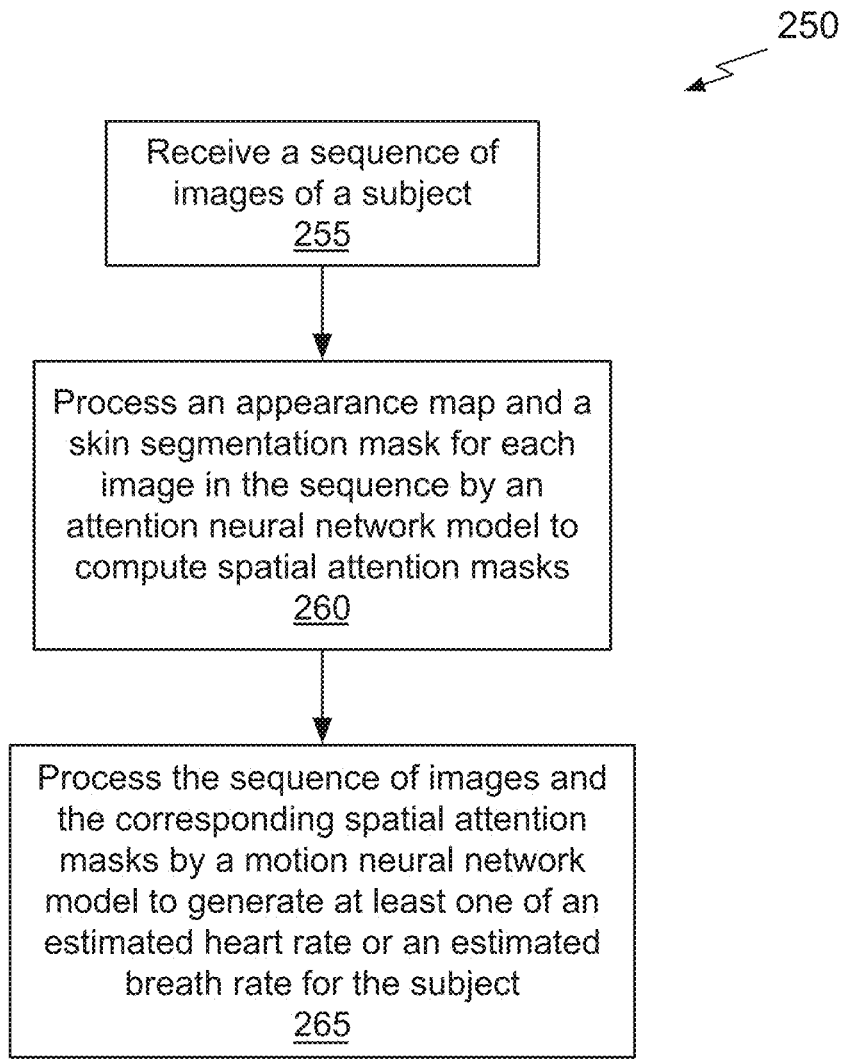
FIG. 2B illustrates a flowchart of another method for joint heart rate and breath rate estimation, in accordance with an embodiment.

FIG. 2B illustrates a flowchart of another method 250 for joint heart rate and breath rate estimation, in accordance with an embodiment. Each block of method 250, described herein, comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a standalone application, a service or hosted service (standalone or in combination with another hosted service), or a plug-in to another product, to name a few. In addition, method 250 is described, by way of example, with respect to the system 200 of FIG. 2A. However, this method may additionally or alternatively be executed by any one system, or any combination of systems, including, but not limited to, those described herein. Furthermore, persons of ordinary skill in the art will understand that any system that performs method 250 is within the scope and spirit of embodiments of the present disclosure.

At step 255, a sequence of images of a subject is received. Each image in the sequence may be processed to generate a motion map, an appearance map, and a skin segmentation mask. At step 260, an appearance map and a skin segmentation mask are processed for each image in the sequence. At step 260, an appearance neural network model processes the appearance map and the skin segmentation mask to compute spatial attention masks. At step 265, the sequence of images and the corresponding spatial attention masks are processed by a motion neural network model to generate at least one of an estimated heart rate or an estimated breath rate for the subject.

Applying (dual) attention in both the spatial domain and channel-wise domain improves accuracy of the joint heart rate and breath rate estimation network systems 100 and 200. Spatial domain attention enhances spatial encoding which locates facial regions that contain strong physiological signal response. Channel-wise domain attention recalibrates channel-wise feature responses to select the most informative features.

Figure 2C:
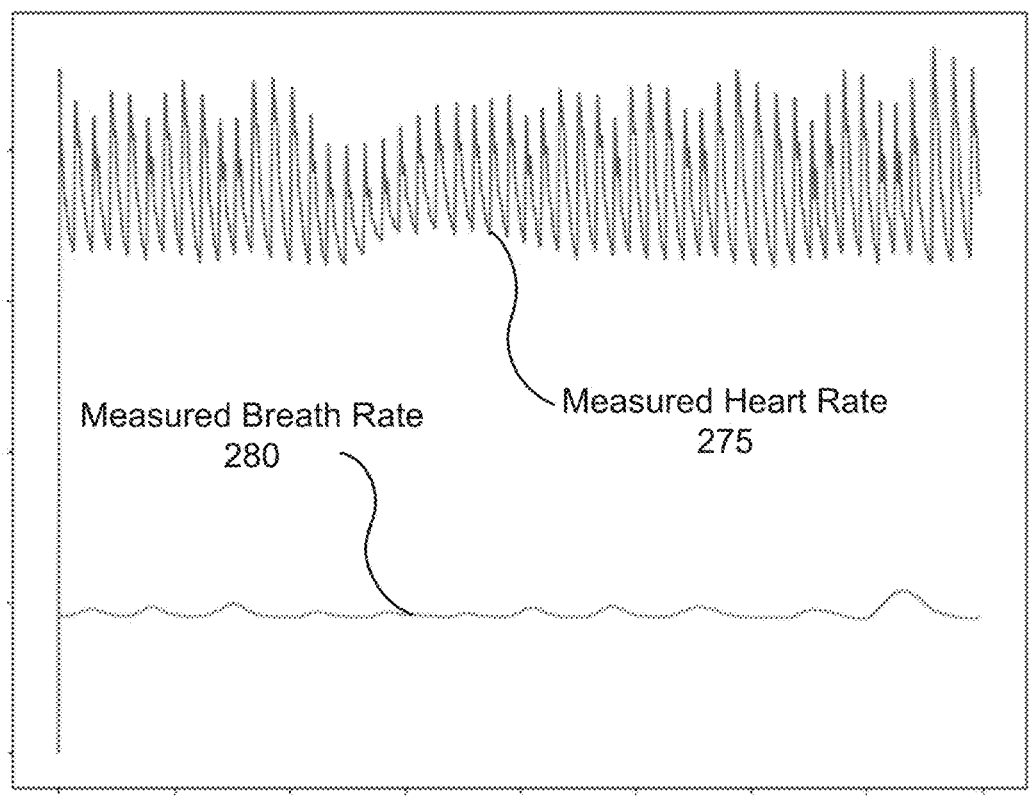
FIG. 2C illustrates a frequency relationship between heart and breathing rates suitable for use in implementing some embodiments of the present disclosure.

The joint heart rate and breath rate estimation network systems 100 and 200 may also rely on a correlation between heart and breath rates to improve accuracy. FIG. 2C illustrates a frequency relationship between heart and breathing rates suitable for use in implementing some embodiments of the present disclosure. For each subject, a measured heart rate 275 has a higher frequency compared with a measured breath rate 280. The relationship between the measured heart rate 275 and measured breath rate 280 is consistent for most subjects. The heart rate and breath rate correlation may be subject specific, and the correlation learned during a system calibration stage may be applied in deployment.

Figure 2D:
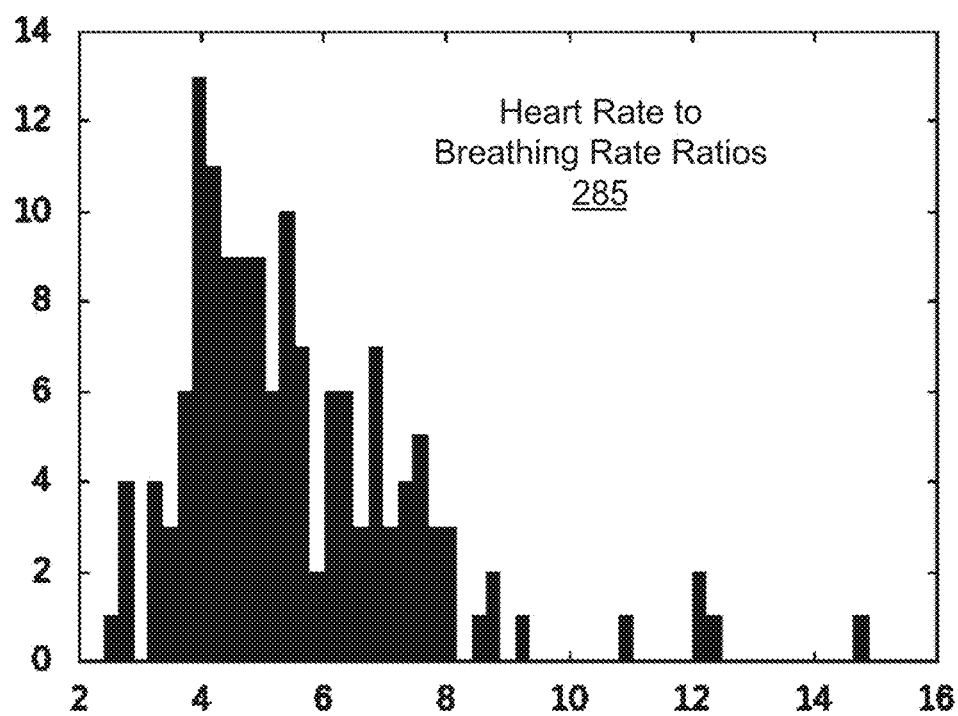
FIG. 2D illustrates a distribution of ratios between heart and breathing rates suitable for use in implementing some embodiments of the present disclosure.

FIG. 2D illustrates a distribution of ratios between heart and breathing rates suitable for use in implementing some embodiments of the present disclosure. A graph of heart rate to breathing rate ratios 285 illustrates that the ratios are clustered around a mean ratio of 5.5655, with a maximum of 14.8333 and a minimum of 2.5417. The standard deviation is 1.9546 with R=0.3000. In an embodiment, during deployment of the joint heart rate and breath rate estimation network systems 100 and 200, the estimated heart rate and the estimated breath rate are discarded (e.g., removed) when a ratio of the estimated heart rate and the estimated breath rate is outside of a predetermined (ground truth) ratio range of heart and breath rates. In an embodiment, false positive heart rate or breath rate estimations are removed by using a signal to noise ratio of heart rate waveform or breath rate waveform to assess the accuracy of the heart rate or breath rate estimates. The signal to noise ratio can be computed in the frequency domain as a ratio between the first two harmonics and remaining frequencies within heart rate or breath rate frequency range. In an embodiment, when the signal to noise ratio is less than zero, the heart rate or breath rate estimation is discarded because the signal is weaker than noise.

During training of the joint heart rate and breath rate estimation network systems 100 and 200, the parameters (e.g., weights) are learned and the channel attentions are also learned. The correlation between the heart and breath rates may be used during training to improve accuracy of the joint heart rate and breath rate estimation network systems 100 and 200. In an embodiment, the heart to breath rate ratio of 4:1~6:1 is used as a ground truth ratio range.

Conventionally, a multitask learning loss L is the summation of heart rate waveform mean squared error (MSE) loss and respiratory rate waveform MSE loss, which is defined as:

$$L = \alpha \frac{1}{T}\sum_{k=1}^{T}(p(t)-p(t)')^2 + \beta \frac{1}{T}\sum_{k=1}^{T}(r(t)-r(t)')^2, \quad \text{Eq. (3)}$$

where T is a time window, p(t) and r(t) are time variant ground truth pulse (e.g., heart rate) waveform sequence and respiratory waveform sequence respectively, p(t)' and r(t)' are predicted pulse waveform and respiratory waveform, $\alpha$, $\beta$ are empirical parameters to balance pulse waveform loss and respiratory waveform loss. In an embodiment, $\alpha=\beta=1$.

The objective or loss function reduces differences between the predicted heart and breath rates and the ground truth heart and breath rates. In an embodiment, a ratio-based correlation loss is included in the loss function:

$$L_{ratio} = \qquad\qquad\qquad\qquad\qquad\qquad\qquad \text{Eq. (4)}$$
$$\alpha\frac{1}{T}\sum_{k=1}^{T}(p(t)-p(t)')^2 + \beta\frac{1}{T}\sum_{k=1}^{T}(r(t)-r(t)')^2 + \gamma(\text{ratio\_diff}),$$

where $\gamma$ is an empirical parameter to control the ratio-based correlation loss and ratio_diff is a difference between a ratio of the predicted heart rate and breath rate and the ground truth ratio range. In an embodiment, the loss function $L_{ratio}$ of Equation (4) gives more penalty if the ratio of the predicted heart rate and breath rate is outside of the ground truth ratio range [4:1, 6:1]. In an embodiment, during training, parameters (e.g., weights) and channel attentions of the joint heart rate and breath rate estimation network systems 100 and 200 are adjusted to reduce differences between ratios of estimated of heart and breath rates and ratios of ground truth heart and breath rates.

In an embodiment, during training, the parameters are adjusted to align correlations between the estimated heart and breath rates with correlations between the ground truth heart and breath rates. In an embodiment, a ratio-based correlation loss and alignment correlation loss are included in the loss function:

$$L_{align} = \alpha\frac{1}{T}\sum_{k=1}^{T}(p(t)-p(t)')^2 + \beta\frac{1}{T}\sum_{k=1}^{T}(r(t)-r(t)')^2 + \gamma L_\rho \quad \text{Eq. (5)}$$

$$L_\rho = 1 - \rho_{p(t)',r(t)'}$$

$$\rho_{p(t)',r(t)'} = \frac{COV(p(t)', r(t)')}{\sigma_{p(t)'}\sigma_{r(t)'}},$$

where $\sigma_{p(t)}$, and $\sigma_{r(t)}$, are the standard deviation of pulse waveform and respiratory waveform respectively, and COV is the covariance.

Figure 3A:
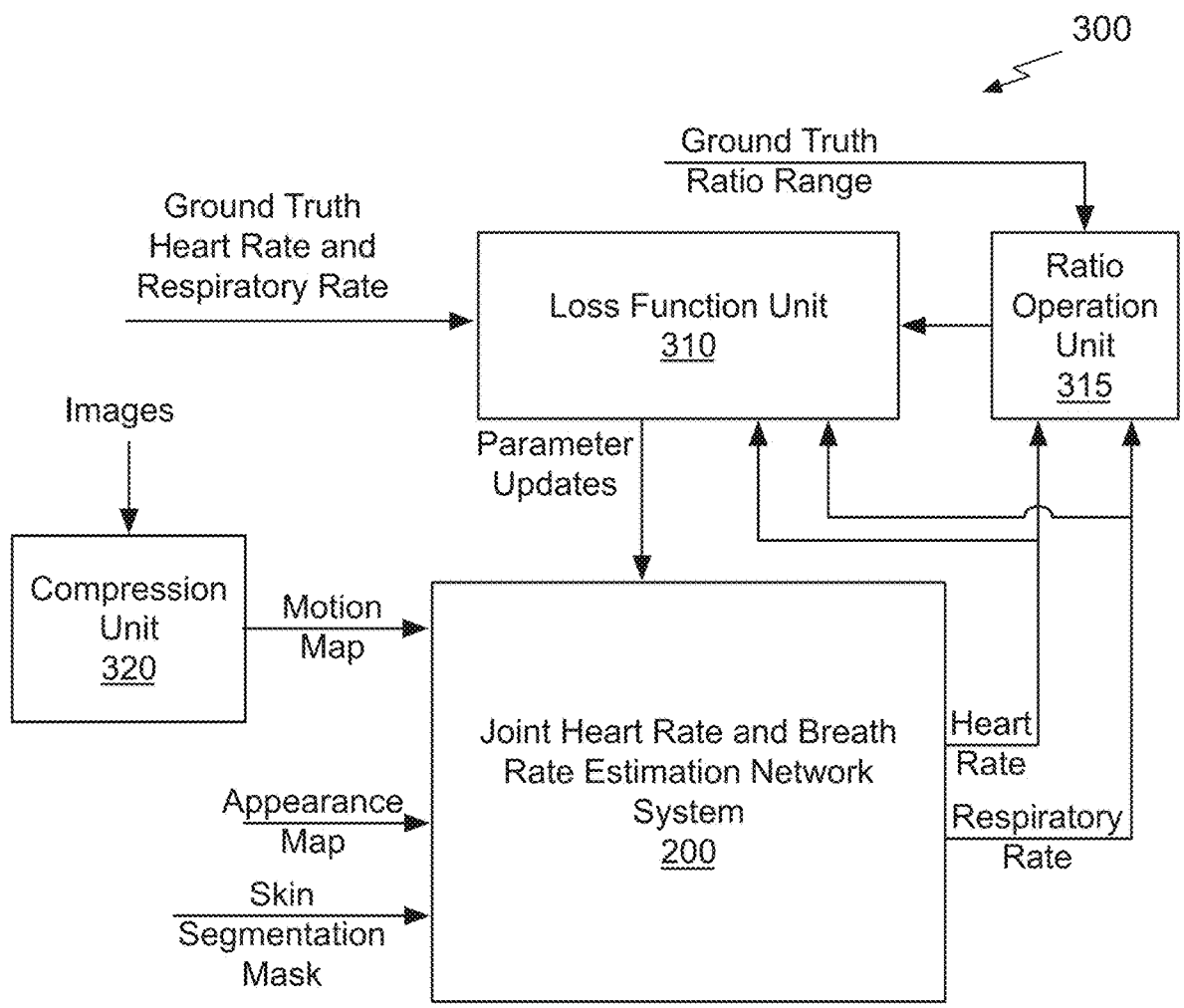
FIG. 3A illustrates a block diagram of a training configuration for the joint heart rate and breath rate estimation network system suitable for use in implementing some embodiments of the present disclosure.

FIG. 3A illustrates a block diagram of a training configuration 300 for the joint heart rate and breath rate estimation network systems 100 and 200 suitable for use in implementing some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the training configuration 300 is within the scope and spirit of embodiments of the present disclosure.

As shown in FIG. 3A, the training configuration 300 includes the joint heart rate and breath rate estimation network system 200, a loss function unit 310, a ratio operation unit 315, and a compression unit 320. The joint heart rate and breath rate estimation network system 100 may be substituted for the joint heart rate and breath rate estimation network system 200. The ratio operation unit 315 computes the heart rate to breath rate ratio and ratio_diff using the predicted heart rate, the predicted respiratory rate, and the ground truth ratio range. The loss function unit 310 receives the predicted heart rate, the predicted respiratory rate, the ratio_diff, and the ground truth heart and respiratory rates. The loss function unit 310 may evaluate one of Equations (3), (4), or (5) to compute parameter updates and update channel attentions for the joint heart rate and breath rate estimation network system 200 via backpropagation.

In some environments, when the joint heart rate and breath rate estimation network system 200 is deployed, the input images may be compressed which typically introduces visual artifacts—making accurate estimation more difficult. The compression level may be variable (i.e., depending on the available bandwidth) or fixed. To improve robustness and generality of the joint heart rate and breath rate estimation network systems 100 and 200, training may use input images that are compressed (or not) at varying levels (e.g., compression ratios). Compression may be effectively employed as a form of data augmentation during training. Therefore, the training configuration 300 may also include the compression unit 320 that receives the images of the subject and optionally compresses each image before computing the motion maps. In an embodiment, the appearance map and skin segmentation mask are also generated using the optionally compressed images. In an embodiment, accuracy of estimations for uncompressed input data does not degrade when the joint heart rate and breath rate estimation network systems 100 and 200 is trained using both uncompressed and multiple levels of compressed input images.

Figure 3B:
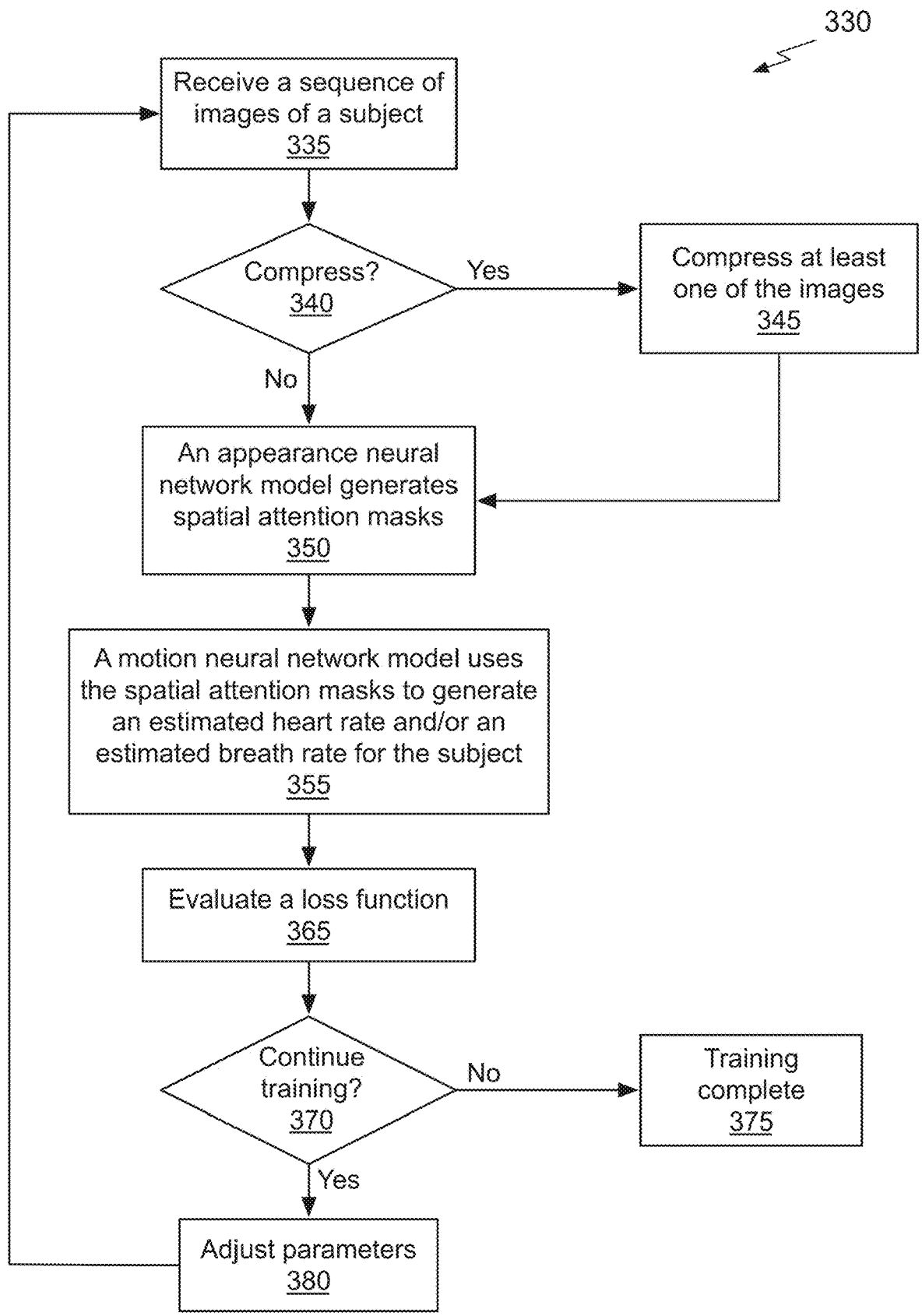
FIG. 3B illustrates another flowchart of a method for training the joint heart rate and breath rate estimation network system suitable for use in implementing some embodiments of the present disclosure.

FIG. 3B illustrates another flowchart of a method 330 for training the joint heart rate and breath rate estimation network system 100 or 200 suitable for use in implementing some embodiments of the present disclosure. Each block of method 330, described herein, comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a standalone application, a service or hosted service (standalone or in combination with another hosted service), or a plug-in to another product, to name a few. In addition, method 330 is described, by way of example, with respect to the joint heart rate and breath rate estimation network system 200 of FIG. 2A. However, this method may additionally or alternatively be executed by any one system, or any combination of systems, including, but not limited to, those described herein. Furthermore, persons of ordinary skill in the art will understand that any system that performs method 330 is within the scope and spirit of embodiments of the present disclosure.

At step 335, a sequence of images of a subject is received. At step 340, the compression unit 320 determines if each image in the sequence is compressed or not. For a portion of the images to be compressed, the compression unit 320 also determines a compression level for each image in the portion, and at step 345, the compression unit 320 compresses each image in the portion before generating one or more of a motion map, an appearance map, and a skin segmentation mask. Step 345 may generate compressed images at the same or varying levels as data augmentation to use uncompressed data as training data, so that the dual-attention joint heart rate and breath rate estimation network system 100 or 200 learns to produce estimations for any compression level. While compression of images or video is conventionally viewed as introducing artifacts in rPPG because compression artifacts corrupt a physiological signal, compression can be used as a training data augmentation technique to improve robustness of the joint heart rate and breath rate estimation network system 100 or 200. Otherwise, for images that are not compressed, the compression unit 320 generates one or more of the motion map, the appearance map, and the skin segmentation mask using the images in uncompressed form.

At step 350, an appearance neural network model, such as the appearance neural network model 235, generates spatial attention masks using each appearance map and skin segmentation mask. At step 355, a motion neural network model uses the spatial attention masks to generate an estimated heart rate and/or an estimated breath rate for the subject. At step 365, a loss function is evaluated based on the estimated heart rate and/or an estimated breath rate. In an embodiment, the loss function unit 310 evaluates the loss function. In an embodiment, a ratio of the estimated heart rate and the estimated breath rate is computed as an input to the loss function. In an embodiment, one of the loss functions computed according to Equation (3), (4), or (5) is evaluated.

At step 370, a determination is made whether training should continue. In an embodiment, training continues if evaluation of the loss function indicates that the loss is greater than a threshold value associated with a desired level of accuracy. If, at step 370, training does not continue, then at step 375 training is complete and the joint heart rate and breath rate estimation network system 100 or 200 may be deployed. Otherwise, at step 380, parameters of the joint heart rate and breath rate estimation network system 100 or 200 are adjusted (e.g., updated). In an embodiment the channel attention maps are also adjusted at step 380.

In an embodiment, the parameters are applied by the layers of the motion neural network model and/or the attention neural network model, and the parameters are adjusted to reduce differences between a ground truth heart rate or breath rate and the estimated heart rate or breath rate. In an embodiment, the parameters are applied by the layers of the motion neural network model and/or the attention neural network model, and the parameters are adjusted to reduce differences between an estimated ratio of the estimated heart rate and the estimated breath rate and ground truth ratio range. In an embodiment, the parameters are applied by the layers of the motion neural network model and/or the attention neural network model, and the parameters are adjusted to increase correlations between the estimated heart rate and the estimated breath rate to align with expected correlations between a heart rate and a breath rate.

There are many use cases for heart and/or breath rate estimation, particularly in automotive, healthcare, and gaming environments. In an automotive environment, the joint heart rate and breath rate estimation network system 100 or 200 may be used to monitor an operator's stress, fatigue, or incapacitation. Based on the estimates, minimum risk maneuvers may be initiated (e.g., change music, modify braking settings, pull over, emergency call, etc.) The joint heart rate and breath rate estimation network system 100 or 200 may also be used to perform child presence detection. In a healthcare environment, the joint heart rate and breath rate estimation network system 100 or 200 may be used for telemedicine or touchless on-site screening. In a gaming environment, the joint heart rate and breath rate estimation network system 100 or 200 may be used to measure a user's level of engagement and/or excitement.

Integration of both spatial attention and channel-wise attention into the convolutional neural network architecture of the motion neural network model and the appearance neural network model improves heart rate and respiratory rate estimation. Specifically, the skin segmentation mask improves accuracy by identifying the facial skin (forehead, cheek, nose, etc.), neck and chest region to provide additional data (e.g., blood circulation) for estimating the heart and breath rates. In contrast, conventional techniques for estimating heart and/or breath rates rely on spatial attention masks and do not use channel-based attention.

Available bandwidth for transferring the sequence of input images may vary, resulting in variable frame rates and/or levels of image compression. When the video frame rate the sequence of input images is dynamic, the heart and breath rates may be adjusted accordingly. Compression augmentation (at varying levels) may be employed during training to improve generality and robustness of the motion neural network model and the appearance neural network model.

Parallel Processing Architecture

Figure 4:
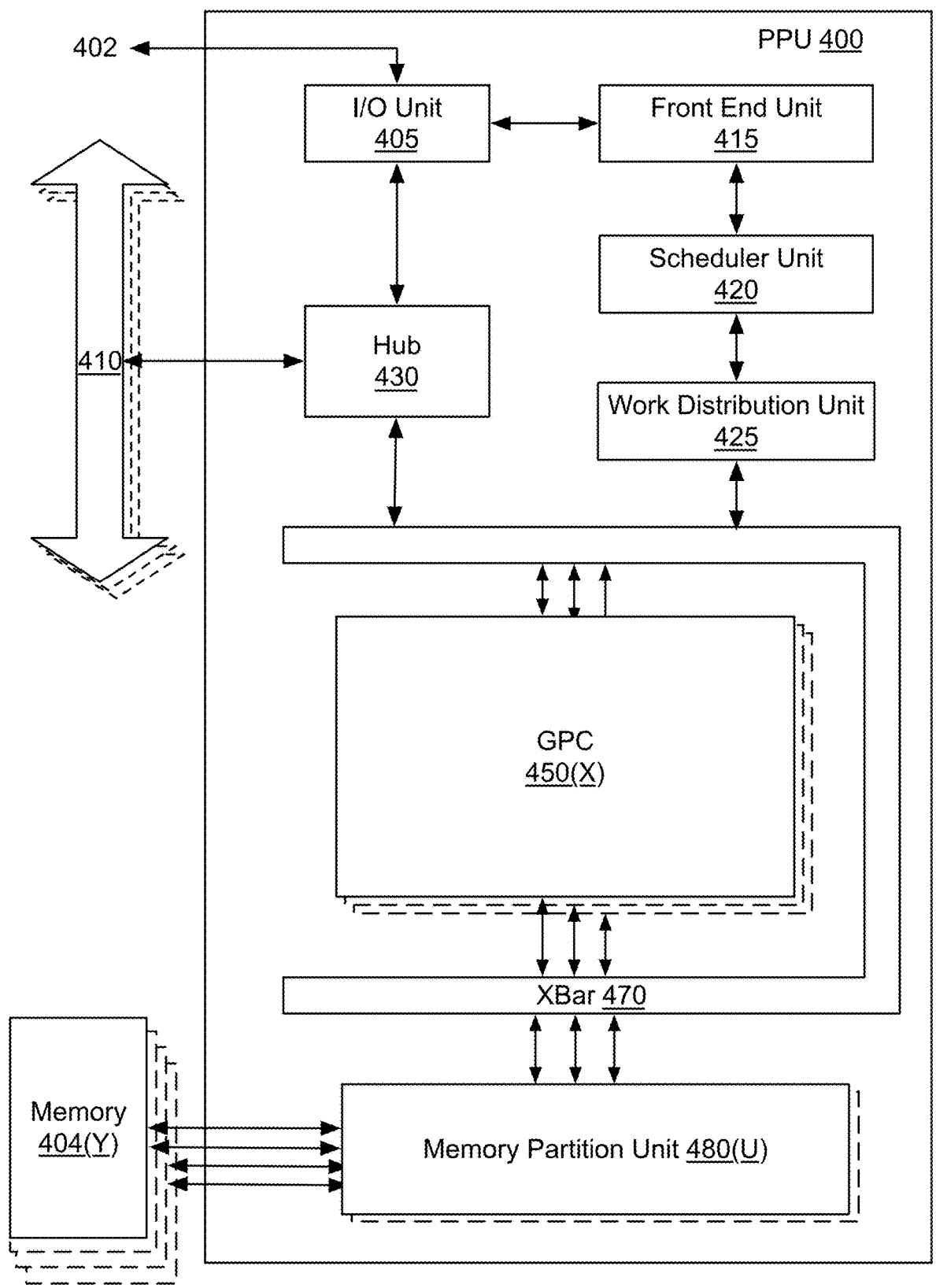
FIG. 4 illustrates an example parallel processing unit suitable for use in implementing some embodiments of the present disclosure.

FIG. 4 illustrates a parallel processing unit (PPU) 400, in accordance with an embodiment. The PPU 400 may be used to implement the joint heart rate and breath rate estimation network system 100 or 200. The PPU 400 may be used to implement one or more of the motion neural network model, the appearance neural network model 235, the loss function unit 310, and the compression unit 320. In an embodiment, a processor such as the PPU 400 may be configured to implement a neural network model. The neural network model may be implemented as software instructions executed by the processor or, in other embodiments, the processor can include a matrix of hardware elements configured to process a set of inputs (e.g., electrical signals representing values) to generate a set of outputs, which can represent activations of the neural network model. In yet other embodiments, the neural network model can be implemented as a combination of software instructions and processing performed by a matrix of hardware elements. Implementing the neural network model can include determining a set of parameters for the neural network model through, e.g., supervised or unsupervised training of the neural network model as well as, or in the alternative, performing inference using the set of parameters to process novel sets of inputs.

In an embodiment, the PPU 400 is a multi-threaded processor that is implemented on one or more integrated circuit devices. The PPU 400 is a latency hiding architecture designed to process many threads in parallel. A thread (e.g., a thread of execution) is an instantiation of a set of instructions configured to be executed by the PPU 400. In an embodiment, the PPU 400 is a graphics processing unit (GPU) configured to implement a graphics rendering pipeline for processing three-dimensional (3D) graphics data in order to generate two-dimensional (2D) image data for display on a display device. In other embodiments, the PPU 400 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

One or more PPUs 400 may be configured to accelerate thousands of High Performance Computing (HPC), data center, cloud computing, and machine learning applications. The PPU 400 may be configured to accelerate numerous deep learning systems and applications for autonomous vehicles, simulation, computational graphics such as ray or path tracing, deep learning, high-accuracy speech, image, and text recognition systems, intelligent video analytics, molecular simulations, drug discovery, disease diagnosis, weather forecasting, big data analytics, astronomy, molecular dynamics simulation, financial modeling, robotics, factory automation, real-time language translation, online search optimizations, and personalized user recommendations, and the like.

As shown in FIG. 4, the PPU 400 includes an Input/Output (I/O) unit 405, a front end unit 415, a scheduler unit 420, a work distribution unit 425, a hub 430, a crossbar (Xbar) 470, one or more general processing clusters (GPCs) 450, and one or more memory partition units 480. The PPU 400 may be connected to a host processor or other PPUs 400 via one or more high-speed NVLink 410 interconnect. The PPU 400 may be connected to a host processor or other peripheral devices via an interconnect 402. The PPU 400 may also be connected to a local memory 404 comprising a number of memory devices. In an embodiment, the local memory may comprise a number of dynamic random access memory (DRAM) devices. The DRAM devices may be configured as a high-bandwidth memory (HBM) subsystem, with multiple DRAM dies stacked within each device.

The NVLink 410 interconnect enables systems to scale and include one or more PPUs 400 combined with one or more CPUs, supports cache coherence between the PPUs 400 and CPUs, and CPU mastering. Data and/or commands may be transmitted by the NVLink 410 through the hub 430 to/from other units of the PPU 400 such as one or more copy engines, a video encoder, a video decoder, a power management unit, etc. (not explicitly shown). The NVLink 410 is described in more detail in conjunction with FIG. 5B.

The I/O unit 405 is configured to transmit and receive communications (e.g., commands, data, etc.) from a host processor (not shown) over the interconnect 402. The I/O unit 405 may communicate with the host processor directly via the interconnect 402 or through one or more intermediate devices such as a memory bridge. In an embodiment, the I/O unit 405 may communicate with one or more other processors, such as one or more the PPUs 400 via the interconnect 402. In an embodiment, the I/O unit 405 implements a Peripheral Component Interconnect Express (PCIe) interface for communications over a PCIe bus and the interconnect 402 is a PCIe bus. In alternative embodiments, the I/O unit 405 may implement other types of well-known interfaces for communicating with external devices.

The I/O unit 405 decodes packets received via the interconnect 402. In an embodiment, the packets represent commands configured to cause the PPU 400 to perform various operations. The I/O unit 405 transmits the decoded commands to various other units of the PPU 400 as the commands may specify. For example, some commands may be transmitted to the front end unit 415. Other commands may be transmitted to the hub 430 or other units of the PPU 400 such as one or more copy engines, a video encoder, a video decoder, a power management unit, etc. (not explicitly shown). In other words, the I/O unit 405 is configured to route communications between and among the various logical units of the PPU 400.

In an embodiment, a program executed by the host processor encodes a command stream in a buffer that provides workloads to the PPU 400 for processing. A workload may comprise several instructions and data to be processed by those instructions. The buffer is a region in a memory that is accessible (e.g., read/write) by both the host processor and the PPU 400. For example, the I/O unit 405 may be configured to access the buffer in a system memory connected to the interconnect 402 via memory requests transmitted over the interconnect 402. In an embodiment, the host processor writes the command stream to the buffer and then transmits a pointer to the start of the command stream to the PPU 400. The front end unit 415 receives pointers to one or more command streams. The front end unit 415 manages the one or more streams, reading commands from the streams and forwarding commands to the various units of the PPU 400.

The front end unit 415 is coupled to a scheduler unit 420 that configures the various GPCs 450 to process tasks defined by the one or more streams. The scheduler unit 420 is configured to track state information related to the various tasks managed by the scheduler unit 420. The state may indicate which GPC 450 a task is assigned to, whether the task is active or inactive, a priority level associated with the task, and so forth. The scheduler unit 420 manages the execution of a plurality of tasks on the one or more GPCs 450.

The scheduler unit 420 is coupled to a work distribution unit 425 that is configured to dispatch tasks for execution on the GPCs 450. The work distribution unit 425 may track a number of scheduled tasks received from the scheduler unit 420. In an embodiment, the work distribution unit 425 manages a pending task pool and an active task pool for each of the GPCs 450. As a GPC 450 finishes the execution of a task, that task is evicted from the active task pool for the GPC 450 and one of the other tasks from the pending task pool is selected and scheduled for execution on the GPC 450. If an active task has been idle on the GPC 450, such as while waiting for a data dependency to be resolved, then the active task may be evicted from the GPC 450 and returned to the pending task pool while another task in the pending task pool is selected and scheduled for execution on the GPC 450.

In an embodiment, a host processor executes a driver kernel that implements an application programming interface (API) that enables one or more applications executing on the host processor to schedule operations for execution on the PPU 400. In an embodiment, multiple compute applications are simultaneously executed by the PPU 400 and the PPU 400 provides isolation, quality of service (QoS), and independent address spaces for the multiple compute applications. An application may generate instructions (e.g., API calls) that cause the driver kernel to generate one or more tasks for execution by the PPU 400. The driver kernel outputs tasks to one or more streams being processed by the PPU 400. Each task may comprise one or more groups of related threads, referred to herein as a warp. In an embodiment, a warp comprises 32 related threads that may be executed in parallel. Cooperating threads may refer to a plurality of threads including instructions to perform the task and that may exchange data through shared memory. The tasks may be allocated to one or more processing units within a GPC 450 and instructions are scheduled for execution by at least one warp.

The work distribution unit 425 communicates with the one or more GPCs 450 via XBar 470. The XBar 470 is an interconnect network that couples many of the units of the PPU 400 to other units of the PPU 400. For example, the XBar 470 may be configured to couple the work distribution unit 425 to a particular GPC 450. Although not shown explicitly, one or more other units of the PPU 400 may also be connected to the XBar 470 via the hub 430.

The tasks are managed by the scheduler unit 420 and dispatched to a GPC 450 by the work distribution unit 425. The GPC 450 is configured to process the task and generate results. The results may be consumed by other tasks within the GPC 450, routed to a different GPC 450 via the XBar 470, or stored in the memory 404. The results can be written to the memory 404 via the memory partition units 480, which implement a memory interface for reading and writing data to/from the memory 404. The results can be transmitted to another PPU 400 or CPU via the NVLink 410. In an embodiment, the PPU 400 includes a number U of memory partition units 480 that is equal to the number of separate and distinct memory devices of the memory 404 coupled to the PPU 400. Each GPC 450 may include a memory management unit to provide translation of virtual addresses into physical addresses, memory protection, and arbitration of memory requests. In an embodiment, the memory management unit provides one or more translation lookaside buffers (TLBs) for performing translation of virtual addresses into physical addresses in the memory 404.

In an embodiment, the memory partition unit 480 includes a Raster Operations (ROP) unit, a level two (L2) cache, and a memory interface that is coupled to the memory 404. The memory interface may implement 32, 64, 128, 1024-bit data buses, or the like, for high-speed data transfer. The PPU 400 may be connected to up to Y memory devices, such as high bandwidth memory stacks or graphics double-data-rate, version 5, synchronous dynamic random access memory, or other types of persistent storage. In an embodiment, the memory interface implements an HBM2 memory interface and Y equals half U. In an embodiment, the HBM2 memory stacks are located on the same physical package as the PPU 400, providing substantial power and area savings compared with conventional GDDR5 SDRAM systems. In an embodiment, each HBM2 stack includes four memory dies and Y equals 4, with each HBM2 stack including two 128-bit channels per die for a total of 8 channels and a data bus width of 1024 bits.

In an embodiment, the memory 404 supports Single-Error Correcting Double-Error Detecting (SECDED) Error Correction Code (ECC) to protect data. ECC provides higher reliability for compute applications that are sensitive to data corruption. Reliability is especially important in large-scale cluster computing environments where PPUs 400 process very large datasets and/or run applications for extended periods.

In an embodiment, the PPU 400 implements a multi-level memory hierarchy. In an embodiment, the memory partition unit 480 supports a unified memory to provide a single unified virtual address space for CPU and PPU 400 memory, enabling data sharing between virtual memory systems. In an embodiment the frequency of accesses by a PPU 400 to memory located on other processors is traced to ensure that memory pages are moved to the physical memory of the PPU 400 that is accessing the pages more frequently. In an embodiment, the NVLink 410 supports address translation services allowing the PPU 400 to directly access a CPU's page tables and providing full access to CPU memory by the PPU 400.

In an embodiment, copy engines transfer data between multiple PPUs 400 or between PPUs 400 and CPUs. The copy engines can generate page faults for addresses that are not mapped into the page tables. The memory partition unit 480 can then service the page faults, mapping the addresses into the page table, after which the copy engine can perform the transfer. In a conventional system, memory is pinned (e.g., non-pageable) for multiple copy engine operations between multiple processors, substantially reducing the available memory. With hardware page faulting, addresses can be passed to the copy engines without worrying if the memory pages are resident, and the copy process is transparent.

Data from the memory 404 or other system memory may be fetched by the memory partition unit 480 and stored in the L2 cache 460, which is located on-chip and is shared between the various GPCs 450. As shown, each memory partition unit 480 includes a portion of the L2 cache associated with a corresponding memory 404. Lower level caches may then be implemented in various units within the GPCs 450. For example, each of the processing units within a GPC 450 may implement a level one (L1) cache. The L1 cache is private memory that is dedicated to a particular processing unit. The L2 cache 460 is coupled to the memory interface 470 and the XBar 470 and data from the L2 cache may be fetched and stored in each of the L1 caches for processing.

In an embodiment, the processing units within each GPC 450 implement a SIMD (Single-Instruction, Multiple-Data) architecture where each thread in a group of threads (e.g., a warp) is configured to process a different set of data based on the same set of instructions. All threads in the group of threads execute the same instructions. In another embodiment, the processing unit implements a SIMT (Single-Instruction, Multiple Thread) architecture where each thread in a group of threads is configured to process a different set of data based on the same set of instructions, but where individual threads in the group of threads are allowed to diverge during execution. In an embodiment, a program counter, call stack, and execution state is maintained for each warp, enabling concurrency between warps and serial execution within warps when threads within the warp diverge. In another embodiment, a program counter, call stack, and execution state is maintained for each individual thread, enabling equal concurrency between all threads, within and between warps. When execution state is maintained for each individual thread, threads executing the same instructions may be converged and executed in parallel for maximum efficiency.

Cooperative Groups is a programming model for organizing groups of communicating threads that allows developers to express the granularity at which threads are communicating, enabling the expression of richer, more efficient parallel decompositions. Cooperative launch APIs support synchronization amongst thread blocks for the execution of parallel algorithms. Conventional programming models provide a single, simple construct for synchronizing cooperating threads: a barrier across all threads of a thread block (e.g., the syncthreads( ) function). However, programmers would often like to define groups of threads at smaller than thread block granularities and synchronize within the defined groups to enable greater performance, design flexibility, and software reuse in the form of collective group-wide function interfaces.

Cooperative Groups enables programmers to define groups of threads explicitly at sub-block (e.g., as small as a single thread) and multi-block granularities, and to perform collective operations such as synchronization on the threads in a cooperative group. The programming model supports clean composition across software boundaries, so that libraries and utility functions can synchronize safely within their local context without having to make assumptions about convergence. Cooperative Groups primitives enable new patterns of cooperative parallelism, including producer-consumer parallelism, opportunistic parallelism, and global synchronization across an entire grid of thread blocks.

Each processing unit includes a large number (e.g., 128, etc.) of distinct processing cores (e.g., functional units) that may be fully-pipelined, single-precision, double-precision, and/or mixed precision and include a floating point arithmetic logic unit and an integer arithmetic logic unit. In an embodiment, the floating point arithmetic logic units implement the IEEE 754-2008 standard for floating point arithmetic. In an embodiment, the cores include 64 single-precision (32-bit) floating point cores, 64 integer cores, 32 double-precision (64-bit) floating point cores, and 8 tensor cores.

Tensor cores configured to perform matrix operations. In particular, the tensor cores are configured to perform deep learning matrix arithmetic, such as GEMM (matrix-matrix multiplication) for convolution operations during neural network training and inferencing. In an embodiment, each tensor core operates on a 4×4 matrix and performs a matrix multiply and accumulate operation D=A×B+C, where A, B, C, and D are 4×4 matrices.

In an embodiment, the matrix multiply inputs A and B may be integer, fixed-point, or floating point matrices, while the accumulation matrices C and D may be integer, fixed-point, or floating point matrices of equal or higher bitwidths. In an embodiment, tensor cores operate on one, four, or eight bit integer input data with 32-bit integer accumulation. The 8-bit integer matrix multiply requires 1024 operations and results in a full precision product that is then accumulated using 32-bit integer addition with the other intermediate products for a 8×8×16 matrix multiply. In an embodiment, tensor Cores operate on 16-bit floating point input data with 32-bit floating point accumulation. The 16-bit floating point multiply requires 64 operations and results in a full precision product that is then accumulated using 32-bit floating point addition with the other intermediate products for a 4×4×4 matrix multiply. In practice, Tensor Cores are used to perform much larger two-dimensional or higher dimensional matrix operations, built up from these smaller elements. An API, such as CUDA 9 C++ API, exposes specialized matrix load, matrix multiply and accumulate, and matrix store operations to efficiently use Tensor Cores from a CUDA-C++ program. At the CUDA level, the warp-level interface assumes 16×16 size matrices spanning all 32 threads of the warp.

Each processing unit may also comprise M special function units (SFUs) that perform special functions (e.g., attribute evaluation, reciprocal square root, and the like). In an embodiment, the SFUs may include a tree traversal unit configured to traverse a hierarchical tree data structure. In an embodiment, the SFUs may include texture unit configured to perform texture map filtering operations. In an embodiment, the texture units are configured to load texture maps (e.g., a 2D array of texels) from the memory 404 and sample the texture maps to produce sampled texture values for use in shader programs executed by the processing unit. In an embodiment, the texture maps are stored in shared memory that may comprise or include an L1 cache. The texture units implement texture operations such as filtering operations using mip-maps (e.g., texture maps of varying levels of detail). In an embodiment, each processing unit includes two texture units.

Each processing unit also comprises N load store units (LSUs) that implement load and store operations between the shared memory and the register file. Each processing unit includes an interconnect network that connects each of the cores to the register file and the LSU to the register file, shared memory. In an embodiment, the interconnect network is a crossbar that can be configured to connect any of the cores to any of the registers in the register file and connect the LSUs to the register file and memory locations in shared memory.

The shared memory is an array of on-chip memory that allows for data storage and communication between the processing units and between threads within a processing unit. In an embodiment, the shared memory comprises 128 KB of storage capacity and is in the path from each of the processing units to the memory partition unit 480. The shared memory can be used to cache reads and writes. One or more of the shared memory, L1 cache, L2 cache, and memory 404 are backing stores.

Combining data cache and shared memory functionality into a single memory block provides the best overall performance for both types of memory accesses. The capacity is usable as a cache by programs that do not use shared memory. For example, if shared memory is configured to use half of the capacity, texture and load/store operations can use the remaining capacity. Integration within the shared memory enables the shared memory to function as a high-throughput conduit for streaming data while simultaneously providing high-bandwidth and low-latency access to frequently reused data.

When configured for general purpose parallel computation, a simpler configuration can be used compared with graphics processing. Specifically, fixed function graphics processing units, are bypassed, creating a much simpler programming model. In the general purpose parallel computation configuration, the work distribution unit 425 assigns and distributes blocks of threads directly to the processing units within the GPCs 450. Threads execute the same program, using a unique thread ID in the calculation to ensure each thread generates unique results, using the processing unit(s) to execute the program and perform calculations, shared memory to communicate between threads, and the LSU to read and write global memory through the shared memory and the memory partition unit 480. When configured for general purpose parallel computation, the processing units can also write commands that the scheduler unit 420 can use to launch new work on the processing units.

The PPUs 400 may each include, and/or be configured to perform functions of, one or more processing cores and/or components thereof, such as Tensor Cores (TCs), Tensor Processing Units (TPUs), Pixel Visual Cores (PVCs), Ray Tracing (RT) Cores, Vision Processing Units (VPUs), Graphics Processing Clusters (GPCs), Texture Processing Clusters (TPCs), Streaming Multiprocessors (SMs), Tree Traversal Units (TTUs), Artificial Intelligence Accelerators (AIAs), Deep Learning Accelerators (DLAs), Arithmetic-Logic Units (ALUs), Application-Specific Integrated Circuits (ASICs), Floating Point Units (FPUs), input/output (I/O) elements, peripheral component interconnect (PCI) or peripheral component interconnect express (PCIe) elements, and/or the like.

The PPU 400 may be included in a desktop computer, a laptop computer, a tablet computer, servers, supercomputers, a smart-phone (e.g., a wireless, hand-held device), personal digital assistant (PDA), a digital camera, a vehicle, a head mounted display, a hand-held electronic device, and the like. In an embodiment, the PPU 400 is embodied on a single semiconductor substrate. In another embodiment, the PPU 400 is included in a system-on-a-chip (SoC) along with one or more other devices such as additional PPUs 400, the memory 404, a reduced instruction set computer (RISC) CPU, a memory management unit (MMU), a digital-to-analog converter (DAC), and the like.

In an embodiment, the PPU 400 may be included on a graphics card that includes one or more memory devices. The graphics card may be configured to interface with a PCIe slot on a motherboard of a desktop computer. In yet another embodiment, the PPU 400 may be an integrated graphics processing unit (iGPU) or parallel processor included in the chipset of the motherboard. In yet another embodiment, the PPU 400 may be realized in reconfigurable hardware. In yet another embodiment, parts of the PPU 400 may be realized in reconfigurable hardware.

Exemplary Computing System

Systems with multiple GPUs and CPUs are used in a variety of industries as developers expose and leverage more parallelism in applications such as artificial intelligence computing. High-performance GPU-accelerated systems with tens to many thousands of compute nodes are deployed in data centers, research facilities, and supercomputers to solve ever larger problems. As the number of processing devices within the high-performance systems increases, the communication and data transfer mechanisms need to scale to support the increased bandwidth.

Figure 5A:
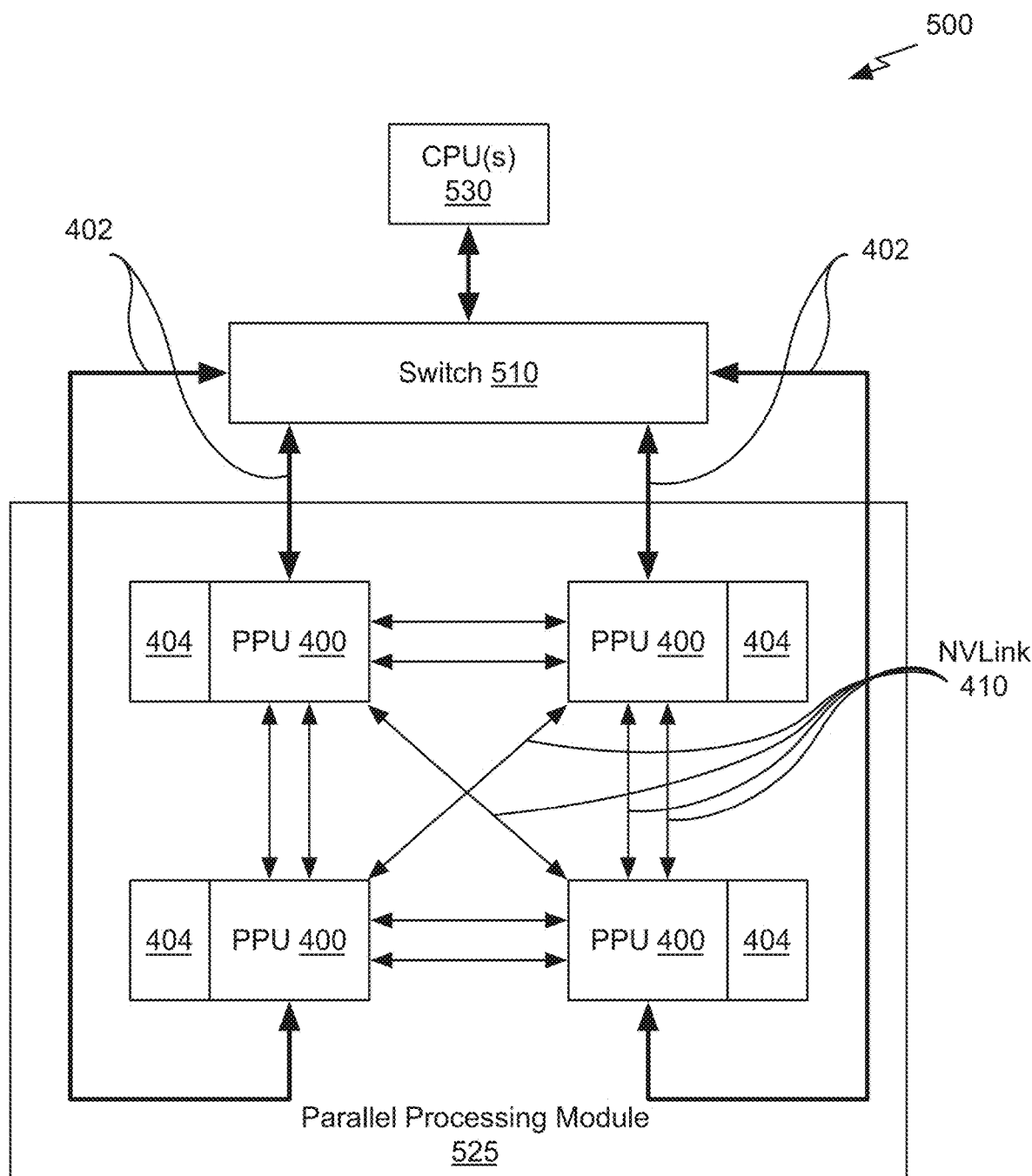
FIG. 5A is a conceptual diagram of a processing system implemented using the PPU of FIG. 4, suitable for use in implementing some embodiments of the present disclosure.

FIG. 5A is a conceptual diagram of a processing system 500 implemented using the PPU 400 of FIG. 4, in accordance with an embodiment. The exemplary system 500 may be configured to implement the method 150, 250, and/or 330 shown in FIGS. 1C, 2B, and/or 3B, respectively. The processing system 500 includes a CPU 530, switch 510, and multiple PPUs 400, and respective memories 404.

Figure 5B:
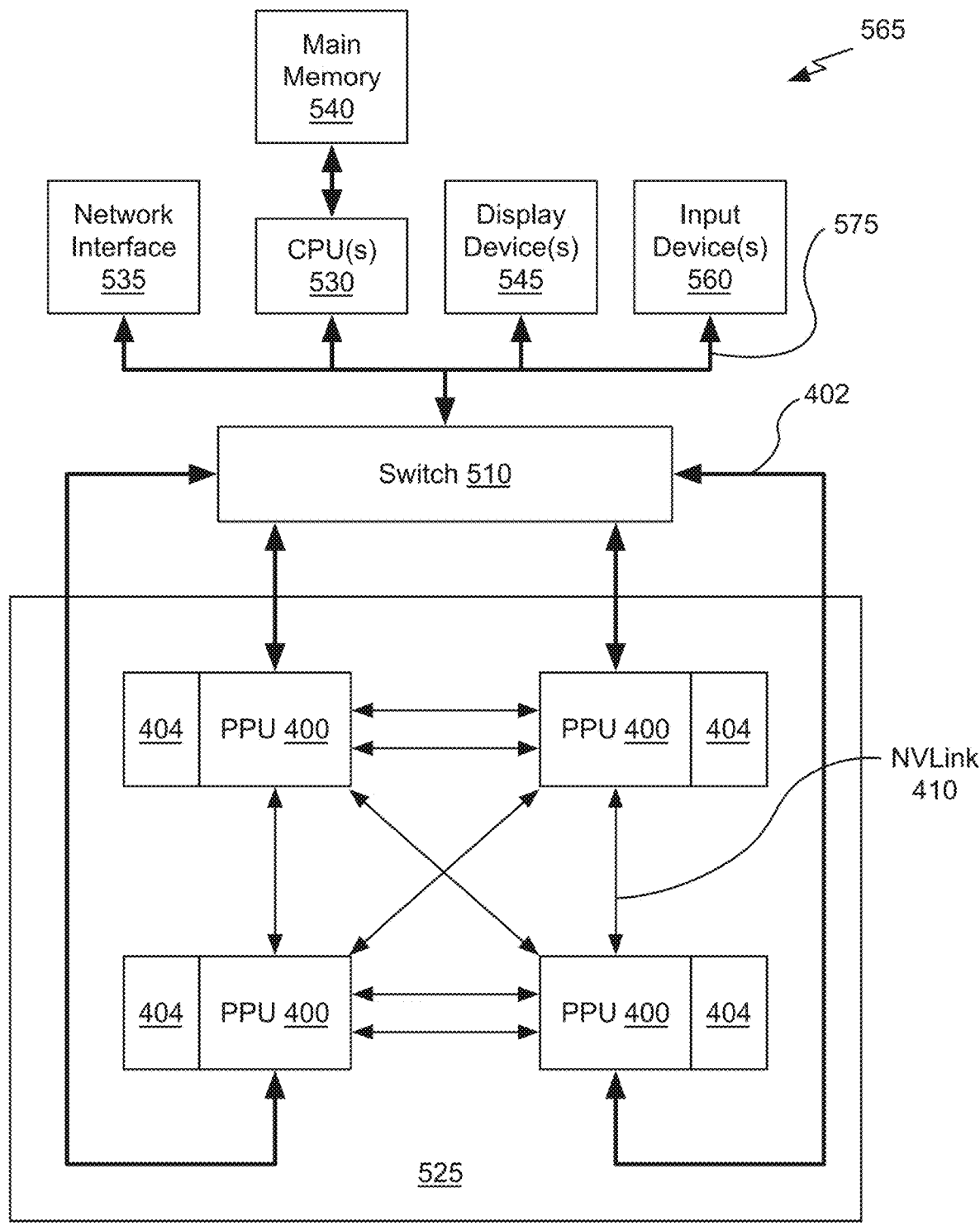
FIG. 5B illustrates an exemplary system in which the various architecture and/or functionality of the various previous embodiments may be implemented.

The NVLink 410 provides high-speed communication links between each of the PPUs 400. Although a particular number of NVLink 410 and interconnect 402 connections are illustrated in FIG. 5B, the number of connections to each PPU 400 and the CPU 530 may vary. The switch 510 interfaces between the interconnect 402 and the CPU 530. The PPUs 400, memories 404, and NVLinks 410 may be situated on a single semiconductor platform to form a parallel processing module 525. In an embodiment, the switch 510 supports two or more protocols to interface between various different connections and/or links.

In another embodiment (not shown), the NVLink 410 provides one or more high-speed communication links between each of the PPUs 400 and the CPU 530 and the switch 510 interfaces between the interconnect 402 and each of the PPUs 400. The PPUs 400, memories 404, and interconnect 402 may be situated on a single semiconductor platform to form a parallel processing module 525. In yet another embodiment (not shown), the interconnect 402 provides one or more communication links between each of the PPUs 400 and the CPU 530 and the switch 510 interfaces between each of the PPUs 400 using the NVLink 410 to provide one or more high-speed communication links between the PPUs 400. In another embodiment (not shown), the NVLink 410 provides one or more high-speed communication links between the PPUs 400 and the CPU 530 through the switch 510. In yet another embodiment (not shown), the interconnect 402 provides one or more communication links between each of the PPUs 400 directly. One or more of the NVLink 410 high-speed communication links may be implemented as a physical NVLink interconnect or either an on-chip or on-die interconnect using the same protocol as the NVLink 410.

In the context of the present description, a single semiconductor platform may refer to a sole unitary semiconductor-based integrated circuit fabricated on a die or chip. It should be noted that the term single semiconductor platform may also refer to multi-chip modules with increased connectivity which simulate on-chip operation and make substantial improvements over utilizing a conventional bus implementation. Of course, the various circuits or devices may also be situated separately or in various combinations of semiconductor platforms per the desires of the user. Alternately, the parallel processing module 525 may be implemented as a circuit board substrate and each of the PPUs 400 and/or memories 404 may be packaged devices. In an embodiment, the CPU 530, switch 510, and the parallel processing module 525 are situated on a single semiconductor platform.

In an embodiment, the signaling rate of each NVLink 410 is 20 to 25 Gigabits/second and each PPU 400 includes six NVLink 410 interfaces (as shown in FIG. 5A, five NVLink 410 interfaces are included for each PPU 400). Each NVLink 410 provides a data transfer rate of 25 Gigabytes/second in each direction, with six links providing 400 Gigabytes/second. The NVLinks 410 can be used exclusively for PPU-to-PPU communication as shown in FIG. 5A, or some combination of PPU-to-PPU and PPU-to-CPU, when the CPU 530 also includes one or more NVLink 410 interfaces.

In an embodiment, the NVLink 410 allows direct load/store/atomic access from the CPU 530 to each PPU's 400 memory 404. In an embodiment, the NVLink 410 supports coherency operations, allowing data read from the memories 404 to be stored in the cache hierarchy of the CPU 530, reducing cache access latency for the CPU 530. In an embodiment, the NVLink 410 includes support for Address Translation Services (ATS), allowing the PPU 400 to directly access page tables within the CPU 530. One or more of the NVLinks 410 may also be configured to operate in a low-power mode.

FIG. 5B illustrates an exemplary system 565 in which the various architecture and/or functionality of the various previous embodiments may be implemented. The exemplary system 565 may be configured to implement the method 150, 250, and/or 330 shown in FIGS. 1C, 2B, and/or 3B, respectively.

As shown, a system 565 is provided including at least one central processing unit 530 that is connected to a communication bus 575. The communication bus 575 may directly or indirectly couple one or more of the following devices: main memory 540, network interface 535, CPU(s) 530, display device(s) 545, input device(s) 560, switch 510, and parallel processing system 525. The communication bus 575 may be implemented using any suitable protocol and may represent one or more links or busses, such as an address bus, a data bus, a control bus, or a combination thereof. The communication bus 575 may include one or more bus or link types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, HyperTransport, and/or another type of bus or link. In some embodiments, there are direct connections between components. As an example, the CPU(s) 530 may be directly connected to the main memory 540. Further, the CPU(s) 530 may be directly connected to the parallel processing system 525. Where there is direct, or point-to-point connection between components, the communication bus 575 may include a PCIe link to carry out the connection. In these examples, a PCI bus need not be included in the system 565.

Although the various blocks of FIG. 5B are shown as connected via the communication bus 575 with lines, this is not intended to be limiting and is for clarity only. For example, in some embodiments, a presentation component, such as display device(s) 545, may be considered an I/O component, such as input device(s) 560 (e.g., if the display is a touch screen). As another example, the CPU(s) 530 and/or parallel processing system 525 may include memory (e.g., the main memory 540 may be representative of a storage device in addition to the parallel processing system 525, the CPUs 530, and/or other components). In other words, the computing device of FIG. 5B is merely illustrative. Distinction is not made between such categories as "workstation," "server," "laptop," "desktop," "tablet," "client device," "mobile device," "hand-held device," "game console," "electronic control unit (ECU)," "virtual reality system," and/or other device or system types, as all are contemplated within the scope of the computing device of FIG. 5B.

The system 565 also includes a main memory 540. Control logic (software) and data are stored in the main memory 540 which may take the form of a variety of computer-readable media. The computer-readable media may be any available media that may be accessed by the system 565. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the main memory 540 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by system 565. As used herein, computer storage media does not comprise signals per se.

The computer storage media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the computer storage media may include wired media such as a wired network or direct-wired connection, and wireless media such as acoustic, RF, infrared and other wireless media. Combinations of any of the above should also be included within the scope of computer-readable media.

Computer programs, when executed, enable the system 565 to perform various functions. The CPU(s) 530 may be configured to execute at least some of the computer-readable instructions to control one or more components of the system 565 to perform one or more of the methods and/or processes described herein. The CPU(s) 530 may each include one or more cores (e.g., one, two, four, eight, twenty-eight, seventy-two, etc.) that are capable of handling a multitude of software threads simultaneously. The CPU(s) 530 may include any type of processor, and may include different types of processors depending on the type of system 565 implemented (e.g., processors with fewer cores for mobile devices and processors with more cores for servers). For example, depending on the type of system 565, the processor may be an Advanced RISC Machines (ARM) processor implemented using Reduced Instruction Set Computing (RISC) or an x86 processor implemented using Complex Instruction Set Computing (CISC). The system 565 may include one or more CPUs 530 in addition to one or more microprocessors or supplementary co-processors, such as math co-processors.

In addition to or alternatively from the CPU(s) 530, the parallel processing module 525 may be configured to execute at least some of the computer-readable instructions to control one or more components of the system 565 to perform one or more of the methods and/or processes described herein. The parallel processing module 525 may be used by the system 565 to render graphics (e.g., 3D graphics) or perform general purpose computations. For example, the parallel processing module 525 may be used for General-Purpose computing on GPUs (GPGPU). In embodiments, the CPU(s) 530 and/or the parallel processing module 525 may discretely or jointly perform any combination of the methods, processes and/or portions thereof.

The system 565 also includes input device(s) 560, the parallel processing system 525, and display device(s) 545. The display device(s) 545 may include a display (e.g., a monitor, a touch screen, a television screen, a heads-up-display (HUD), other display types, or a combination thereof), speakers, and/or other presentation components. The display device(s) 545 may receive data from other components (e.g., the parallel processing system 525, the CPU(s) 530, etc.), and output the data (e.g., as an image, video, sound, etc.).

The network interface 535 may enable the system 565 to be logically coupled to other devices including the input devices 560, the display device(s) 545, and/or other components, some of which may be built in to (e.g., integrated in) the system 565. Illustrative input devices 560 include a microphone, mouse, keyboard, joystick, game pad, game controller, satellite dish, scanner, printer, wireless device, etc. The input devices 560 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the system 565. The system 565 may be include depth cameras, such as stereoscopic camera systems, infrared camera systems, RGB camera systems, touchscreen technology, and combinations of these, for gesture detection and recognition. Additionally, the system 565 may include accelerometers or gyroscopes (e.g., as part of an inertia measurement unit (IMU)) that enable detection of motion. In some examples, the output of the accelerometers or gyroscopes may be used by the system 565 to render immersive augmented reality or virtual reality.

Further, the system 565 may be coupled to a network (e.g., a telecommunications network, local area network (LAN), wireless network, wide area network (WAN) such as the Internet, peer-to-peer network, cable network, or the like) through a network interface 535 for communication purposes. The system 565 may be included within a distributed network and/or cloud computing environment.

The network interface 535 may include one or more receivers, transmitters, and/or transceivers that enable the system 565 to communicate with other computing devices via an electronic communication network, included wired and/or wireless communications. The network interface 535 may be implemented as a network interface controller (NIC) that includes one or more data processing units (DPUs) to perform operations such as (for example and without limitation) packet parsing and accelerating network processing and communication. The network interface 535 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet or InfiniBand), low-power wide-area networks (e.g., LoRaWAN, SigFox, etc.), and/or the Internet.

The system 565 may also include a secondary storage (not shown). The secondary storage includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner. The system 565 may also include a hard-wired power supply, a battery power supply, or a combination thereof (not shown). The power supply may provide power to the system 565 to enable the components of the system 565 to operate.

Each of the foregoing modules and/or devices may even be situated on a single semiconductor platform to form the system 565. Alternately, the various modules may also be situated separately or in various combinations of semiconductor platforms per the desires of the user. While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

Example Network Environments

Network environments suitable for use in implementing embodiments of the disclosure may include one or more client devices, servers, network attached storage (NAS), other backend devices, and/or other device types. The client devices, servers, and/or other device types (e.g., each device) may be implemented on one or more instances of the processing system 500 of FIG. 5A and/or exemplary system 565 of FIG. 5B—e.g., each device may include similar components, features, and/or functionality of the processing system 500 and/or exemplary system 565.

Components of a network environment may communicate with each other via a network(s), which may be wired, wireless, or both. The network may include multiple networks, or a network of networks. By way of example, the network may include one or more Wide Area Networks (WANs), one or more Local Area Networks (LANs), one or more public networks such as the Internet and/or a public switched telephone network (PSTN), and/or one or more private networks. Where the network includes a wireless telecommunications network, components such as a base station, a communications tower, or even access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In embodiments, one or more of the client devices may use the web-based service software or applications (e.g., by accessing the service software and/or applications via one or more application programming interfaces (APIs)). The framework layer may be, but is not limited to, a type of free and open-source software web application framework such as that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). If a connection to a user (e.g., a client device) is relatively close to an edge server(s), a core server(s) may designate at least a portion of the functionality to the edge server(s). A cloud-based network environment may be private (e.g., limited to a single organization), may be public (e.g., available to many organizations), and/or a combination thereof (e.g., a hybrid cloud environment).

The client device(s) may include at least some of the components, features, and functionality of the example processing system 500 of FIG. 5A and/or exemplary system 565 of FIG. 5B. By way of example and not limitation, a client device may be embodied as a Personal Computer (PC), a laptop computer, a mobile device, a smartphone, a tablet computer, a smart watch, a wearable computer, a Personal Digital Assistant (PDA), an MP3 player, a virtual reality headset, a Global Positioning System (GPS) or device, a video player, a video camera, a surveillance device or system, a vehicle, a boat, a flying vessel, a virtual machine, a drone, a robot, a handheld communications device, a hospital device, a gaming device or system, an entertainment system, a vehicle computer system, an embedded system controller, a remote control, an appliance, a consumer electronic device, a workstation, an edge device, any combination of these delineated devices, or any other suitable device.

Machine Learning

Deep neural networks (DNNs) developed on processors, such as the PPU 400 have been used for diverse use cases, from self-driving cars to faster drug development, from automatic image captioning in online image databases to smart real-time language translation in video chat applications. Deep learning is a technique that models the neural learning process of the human brain, continually learning, continually getting smarter, and delivering more accurate results more quickly over time. A child is initially taught by an adult to correctly identify and classify various shapes, eventually being able to identify shapes without any coaching. Similarly, a deep learning or neural learning system needs to be trained in object recognition and classification for it get smarter and more efficient at identifying basic objects, occluded objects, etc., while also assigning context to objects.

At the simplest level, neurons in the human brain look at various inputs that are received, importance levels are assigned to each of these inputs, and output is passed on to other neurons to act upon. An artificial neuron or perceptron is the most basic model of a neural network. In one example, a perceptron may receive one or more inputs that represent various features of an object that the perceptron is being trained to recognize and classify, and each of these features is assigned a certain weight based on the importance of that feature in defining the shape of an object.

A deep neural network (DNN) model includes multiple layers of many connected nodes (e.g., perceptrons, Boltzmann machines, radial basis functions, convolutional layers, etc.) that can be trained with enormous amounts of input data to quickly solve complex problems with high accuracy. In one example, a first layer of the DNN model breaks down an input image of an automobile into various sections and looks for basic patterns such as lines and angles. The second layer assembles the lines to look for higher level patterns such as wheels, windshields, and mirrors. The next layer identifies the type of vehicle, and the final few layers generate a label for the input image, identifying the model of a specific automobile brand.

Once the DNN is trained, the DNN can be deployed and used to identify and classify objects or patterns in a process known as inference. Examples of inference (the process through which a DNN extracts useful information from a given input) include identifying handwritten numbers on checks deposited into ATM machines, identifying images of friends in photos, delivering movie recommendations to over fifty million users, identifying and classifying different types of automobiles, pedestrians, and road hazards in driverless cars, or translating human speech in real-time.

During training, data flows through the DNN in a forward propagation phase until a prediction is produced that indicates a label corresponding to the input. If the neural network does not correctly label the input, then errors between the correct label and the predicted label are analyzed, and the weights are adjusted for each feature during a backward propagation phase until the DNN correctly labels the input and other inputs in a training dataset. Training complex neural networks requires massive amounts of parallel computing performance, including floating-point multiplications and additions that are supported by the PPU 400. Inferencing is less compute-intensive than training, being a latency-sensitive process where a trained neural network is applied to new inputs it has not seen before to classify images, detect emotions, identify recommendations, recognize and translate speech, and generally infer new information.

Neural networks rely heavily on matrix math operations, and complex multi-layered networks require tremendous amounts of floating-point performance and bandwidth for both efficiency and speed. With thousands of processing cores, optimized for matrix math operations, and delivering tens to hundreds of TFLOPS of performance, the PPU 400 is a computing platform capable of delivering performance required for deep neural network-based artificial intelligence and machine learning applications.

Furthermore, data such as images, predicted heart rates, and/or predicted breath rates generated applying one or more of the techniques disclosed herein may be used to train, test, or certify DNNs used to recognize objects and environments in the real world. Such data may include scenes of roadways, factories, buildings, urban settings, rural settings, humans, animals, and any other physical object or real-world setting. Such data may be used to train, test, or certify DNNs that are employed in machines or robots to manipulate, handle, or modify physical objects in the real world. Furthermore, such data may be used to train, test, or certify DNNs that are employed in autonomous vehicles to navigate and move the vehicles through the real world. Additionally, data generated applying one or more of the techniques disclosed herein may be used to convey information to users of such machines, robots, and vehicles.

Figure 5C:
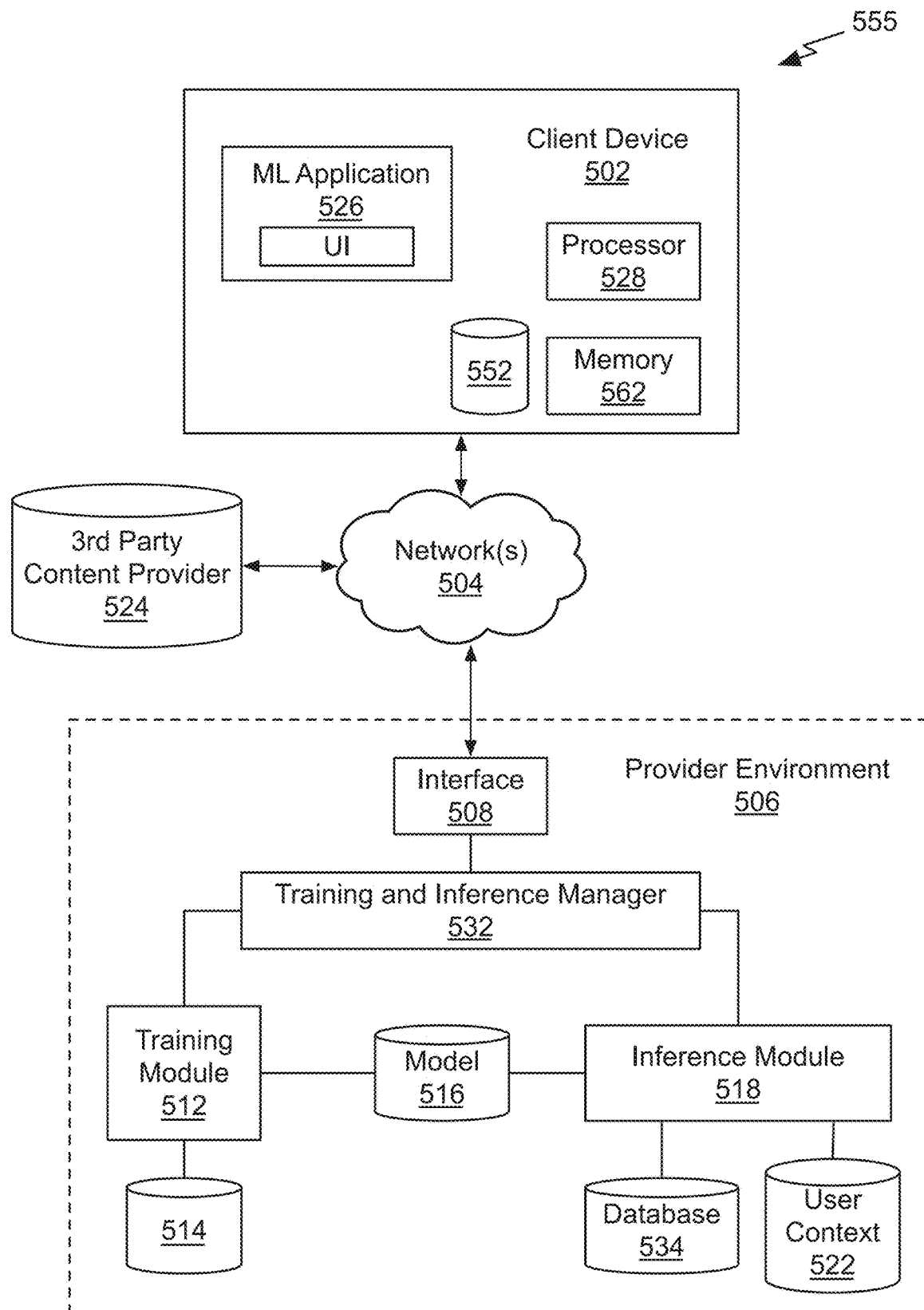
FIG. 5C illustrates components of an exemplary system that can be used to train and utilize machine learning, in at least one embodiment.

FIG. 5C illustrates components of an exemplary system 555 that can be used to train and utilize machine learning, in accordance with at least one embodiment. As will be discussed, various components can be provided by various combinations of computing devices and resources, or a single computing system, which may be under control of a single entity or multiple entities. Further, aspects may be triggered, initiated, or requested by different entities. In at least one embodiment training of a neural network might be instructed by a provider associated with provider environment 506, while in at least one embodiment training might be requested by a customer or other user having access to a provider environment through a client device 502 or other such resource. In at least one embodiment, training data (or data to be analyzed by a trained neural network) can be provided by a provider, a user, or a third party content provider 524. In at least one embodiment, client device 502 may be a vehicle or object that is to be navigated on behalf of a user, for example, which can submit requests and/or receive instructions that assist in navigation of a device.

In at least one embodiment, requests are able to be submitted across at least one network 504 to be received by a provider environment 506. In at least one embodiment, a client device may be any appropriate electronic and/or computing devices enabling a user to generate and send such requests, such as, but not limited to, desktop computers, notebook computers, computer servers, smartphones, tablet computers, gaming consoles (portable or otherwise), computer processors, computing logic, and set-top boxes. Network(s) 504 can include any appropriate network for transmitting a request or other such data, as may include Internet, an intranet, an Ethernet, a cellular network, a local area network (LAN), a wide area network (WAN), a personal area network (PAN), an ad hoc network of direct wireless connections among peers, and so on.

In at least one embodiment, requests can be received at an interface layer 508, which can forward data to a training and inference manager 532, in this example. The training and inference manager 532 can be a system or service including hardware and software for managing requests and service corresponding data or content, in at least one embodiment, the training and inference manager 532 can receive a request to train a neural network, and can provide data for a request to a training module 512. In at least one embodiment, training module 512 can select an appropriate model or neural network to be used, if not specified by the request, and can train a model using relevant training data. In at least one embodiment, training data can be a batch of data stored in a training data repository 514, received from client device 502, or obtained from a third party provider 524. In at least one embodiment, training module 512 can be responsible for training data. A neural network can be any appropriate network, such as a recurrent neural network (RNN) or convolutional neural network (CNN). Once a neural network is trained and successfully evaluated, a trained neural network can be stored in a model repository 516, for example, that may store different models or networks for users, applications, or services, etc. In at least one embodiment, there may be multiple models for a single application or entity, as may be utilized based on a number of different factors.

In at least one embodiment, at a subsequent point in time, a request may be received from client device 502 (or another such device) for content (e.g., path determinations) or data that is at least partially determined or impacted by a trained neural network. This request can include, for example, input data to be processed using a neural network to obtain one or more inferences or other output values, classifications, or predictions, or for at least one embodiment, input data can be received by interface layer 508 and directed to inference module 518, although a different system or service can be used as well. In at least one embodiment, inference module 518 can obtain an appropriate trained network, such as a trained deep neural network (DNN) as discussed herein, from model repository 516 if not already stored locally to inference module 518. Inference module 518 can provide data as input to a trained network, which can then generate one or more inferences as output. This may include, for example, a classification of an instance of input data. In at least one embodiment, inferences can then be transmitted to client device 502 for display or other communication to a user. In at least one embodiment, context data for a user may also be stored to a user context data repository 522, which may include data about a user which may be useful as input to a network in generating inferences, or determining data to return to a user after obtaining instances. In at least one embodiment, relevant data, which may include at least some of input or inference data, may also be stored to a local database 534 for processing future requests. In at least one embodiment, a user can use account information or other information to access resources or functionality of a provider environment. In at least one embodiment, if permitted and available, user data may also be collected and used to further train models, in order to provide more accurate inferences for future requests. In at least one embodiment, requests may be received through a user interface to a machine learning application 526 executing on client device 502, and results displayed through a same interface. A client device can include resources such as a processor 528 and memory 562 for generating a request and processing results or a response, as well as at least one data storage element 552 for storing data for machine learning application 526.

In at least one embodiment a processor 528 (or a processor of training module 512 or inference module 518) will be a central processing unit (CPU). As mentioned, however, resources in such environments can utilize GPUs to process data for at least certain types of requests. With thousands of cores, GPUs, such as PPU 300 are designed to handle substantial parallel workloads and, therefore, have become popular in deep learning for training neural networks and generating predictions. While use of GPUs for offline builds has enabled faster training of larger and more complex models, generating predictions offline implies that either request-time input features cannot be used or predictions must be generated for all permutations of features and stored in a lookup table to serve real-time requests. If a deep learning framework supports a CPU-mode and a model is small and simple enough to perform a feed-forward on a CPU with a reasonable latency, then a service on a CPU instance could host a model. In this case, training can be done offline on a GPU and inference done in real-time on a CPU. If a CPU approach is not viable, then a service can run on a GPU instance. Because GPUs have different performance and cost characteristics than CPUs, however, running a service that offloads a runtime algorithm to a GPU can require it to be designed differently from a CPU based service.

In at least one embodiment, video data can be provided from client device 502 for enhancement in provider environment 506. In at least one embodiment, video data can be processed for enhancement on client device 502. In at least one embodiment, video data may be streamed from a third party content provider 524 and enhanced by third party content provider 524, provider environment 506, or client device 502. In at least one embodiment, video data can be provided from client device 502 for use as training data in provider environment 506.

In at least one embodiment, supervised and/or unsupervised training can be performed by the client device 502 and/or the provider environment 506. In at least one embodiment, a set of training data 514 (e.g., classified or labeled data) is provided as input to function as training data. In at least one embodiment, training data can include instances of at least one type of object for which a neural network is to be trained, as well as information that identifies that type of object. In at least one embodiment, training data might include a set of images that each includes a representation of a type of object, where each image also includes, or is associated with, a label, metadata, classification, or other piece of information identifying a type of object represented in a respective image. Various other types of data may be used as training data as well, as may include text data, audio data, video data, and so on. In at least one embodiment, training data 514 is provided as training input to a training module 512. In at least one embodiment, training module 512 can be a system or service that includes hardware and software, such as one or more computing devices executing a training application, for training a neural network (or other model or algorithm, etc.). In at least one embodiment, training module 512 receives an instruction or request indicating a type of model to be used for training, in at least one embodiment, a model can be any appropriate statistical model, network, or algorithm useful for such purposes, as may include an artificial neural network, deep learning algorithm, learning classifier, Bayesian network, and so on. In at least one embodiment, training module 512 can select an initial model, or other untrained model, from an appropriate repository 516 and utilize training data 514 to train a model, thereby generating a trained model (e.g., trained deep neural network) that can be used to classify similar types of data, or generate other such inferences. In at least one embodiment where training data is not used, an appropriate initial model can still be selected for training on input data per training module 512.

In at least one embodiment, a model can be trained in a number of different ways, as may depend in part upon a type of model selected. In at least one embodiment, a machine learning algorithm can be provided with a set of training data, where a model is a model artifact created by a training process. In at least one embodiment, each instance of training data contains a correct answer (e.g., classification), which can be referred to as a target or target attribute. In at least one embodiment, a learning algorithm finds patterns in training data that map input data attributes to a target, an answer to be predicted, and a machine learning model is output that captures these patterns. In at least one embodiment, a machine learning model can then be used to obtain predictions on new data for which a target is not specified.

In at least one embodiment, training and inference manager 532 can select from a set of machine learning models including binary classification, multiclass classification, generative, and regression models. In at least one embodiment, a type of model to be used can depend at least in part upon a type of target to be predicted.

In an embodiment, the PPU 400 comprises a graphics processing unit (GPU). The PPU 400 is configured to receive commands that specify shader programs for processing graphics data. Graphics data may be defined as a set of primitives such as points, lines, triangles, quads, triangle strips, and the like. Typically, a primitive includes data that specifies a number of vertices for the primitive (e.g., in a model-space coordinate system) as well as attributes associated with each vertex of the primitive. The PPU 400 can be configured to process the graphics primitives to generate a frame buffer (e.g., pixel data for each of the pixels of the display).

An application writes model data for a scene (e.g., a collection of vertices and attributes) to a memory such as a system memory or memory 404. The model data defines each of the objects that may be visible on a display. The application then makes an API call to the driver kernel that requests the model data to be rendered and displayed. The driver kernel reads the model data and writes commands to the one or more streams to perform operations to process the model data. The commands may reference different shader programs to be implemented on the processing units within the PPU 400 including one or more of a vertex shader, hull shader, domain shader, geometry shader, and a pixel shader. For example, one or more of the processing units may be configured to execute a vertex shader program that processes a number of vertices defined by the model data. In an embodiment, the different processing units may be configured to execute different shader programs concurrently. For example, a first subset of processing units may be configured to execute a vertex shader program while a second subset of processing units may be configured to execute a pixel shader program. The first subset of processing units processes vertex data to produce processed vertex data and writes the processed vertex data to the L2 cache 460 and/or the memory 404. After the processed vertex data is rasterized (e.g., transformed from three-dimensional data into two-dimensional data in screen space) to produce fragment data, the second subset of processing units executes a pixel shader to produce processed fragment data, which is then blended with other processed fragment data and written to the frame buffer in memory 404. The vertex shader program and pixel shader program may execute concurrently, processing different data from the same scene in a pipelined fashion until all of the model data for the scene has been rendered to the frame buffer. Then, the contents of the frame buffer are transmitted to a display controller for display on a display device.

Data such as images, predicted heart rates, and/or predicted breath rates generated applying one or more of the techniques disclosed herein may be displayed on a monitor or other display device. In some embodiments, the display device may be coupled directly to the system or processor generating or rendering the images. In other embodiments, the display device may be coupled indirectly to the system or processor such as via a network. Examples of such networks include the Internet, mobile telecommunications networks, a WIFI network, as well as any other wired and/or wireless networking system. When the display device is indirectly coupled, the data generated by the system or processor may be streamed over the network to the display device. Such streaming allows, for example, video games or other applications, which render images, to be executed on a server, a data center, or in a cloud-based computing environment and the rendered images to be transmitted and displayed on one or more user devices (such as a computer, video game console, smartphone, other mobile device, etc.) that are physically separate from the server or data center. Hence, the techniques disclosed herein can be applied to enhance the images that are streamed and to enhance services that stream images such as NVIDIA GeForce Now (GFN), Google Stadia, and the like.

Example Streaming System

Figure 6:
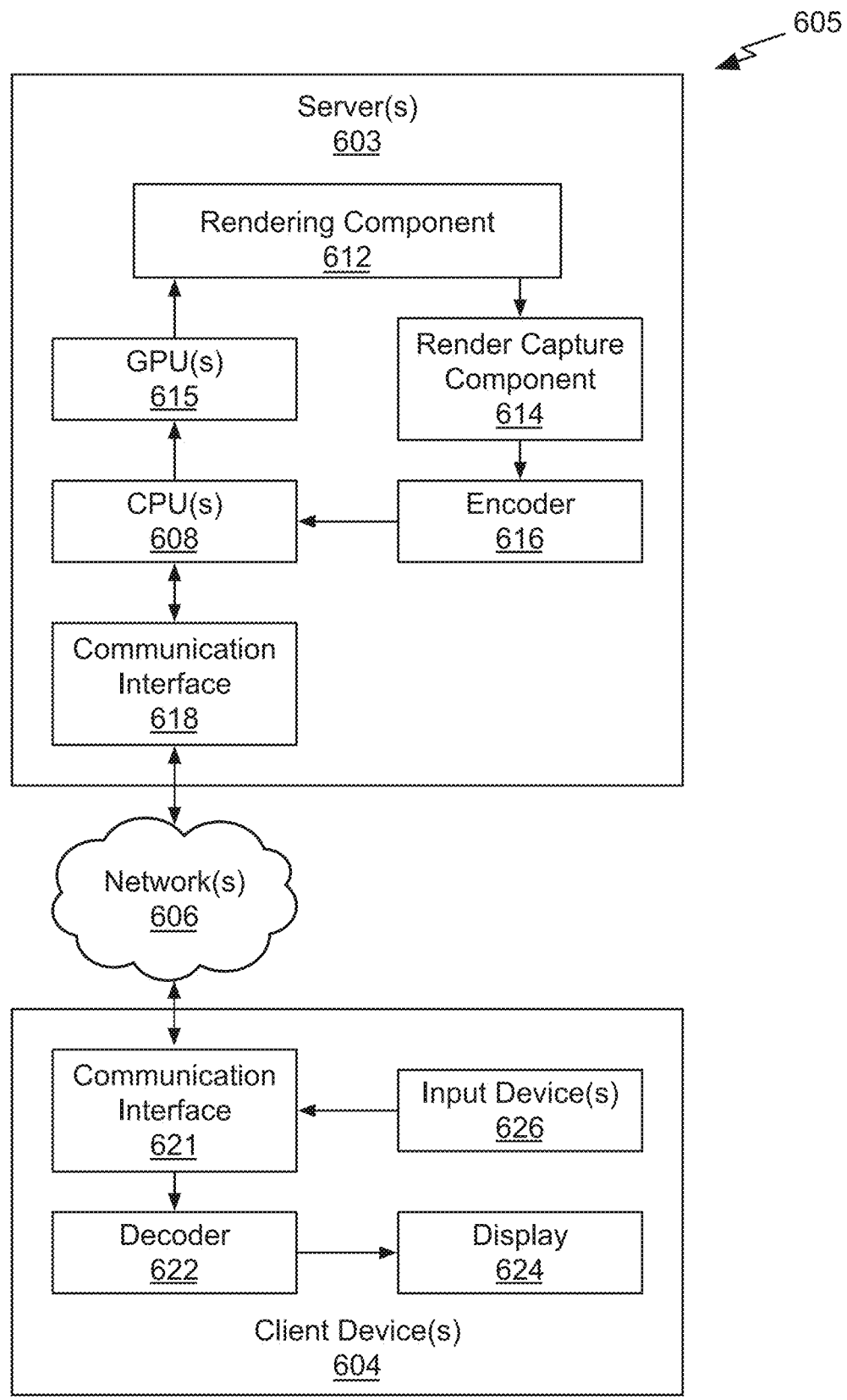
FIG. 6 illustrates an exemplary streaming system suitable for use in implementing some embodiments of the present disclosure.

FIG. 6 is an example system diagram for a streaming system 605, in accordance with some embodiments of the present disclosure. FIG. 6 includes server(s) 603 (which may include similar components, features, and/or functionality to the example processing system 500 of FIG. 5A and/or exemplary system 565 of FIG. 5B), client device(s) 604 (which may include similar components, features, and/or functionality to the example processing system 500 of FIG. 5A and/or exemplary system 565 of FIG. 5B), and network(s) 606 (which may be similar to the network(s) described herein). In some embodiments of the present disclosure, the system 605 may be implemented.

In an embodiment, the streaming system 605 is a game streaming system and the sever(s) 604 are game server(s). In the system 605, for a game session, the client device(s) 604 may only receive input data in response to inputs to the input device(s) 626, transmit the input data to the server(s) 603, receive encoded display data from the server(s) 603, and display the display data on the display 624. As such, the more computationally intense computing and processing is offloaded to the server(s) 603 (e.g., rendering—in particular ray or path tracing—for graphical output of the game session is executed by the GPU(s) 615 of the server(s) 603). In other words, the game session is streamed to the client device(s) 604 from the server(s) 603, thereby reducing the requirements of the client device(s) 604 for graphics processing and rendering.

For example, with respect to an instantiation of a game session, a client device 604 may be displaying a frame of the game session on the display 624 based on receiving the display data from the server(s) 603. The client device 604 may receive an input to one of the input device(s) 626 and generate input data in response. The client device 604 may transmit the input data to the server(s) 603 via the communication interface 621 and over the network(s) 606 (e.g., the Internet), and the server(s) 603 may receive the input data via the communication interface 618. The CPU(s) 608 may receive the input data, process the input data, and transmit data to the GPU(s) 615 that causes the GPU(s) 615 to generate a rendering of the game session. For example, the input data may be representative of a movement of a character of the user in a game, firing a weapon, reloading, passing a ball, turning a vehicle, etc. The rendering component 612 may render the game session (e.g., representative of the result of the input data) and the render capture component 614 may capture the rendering of the game session as display data (e.g., as image data capturing the rendered frame of the game session). The rendering of the game session may include ray or path-traced lighting and/or shadow effects, computed using one or more parallel processing units—such as GPUs, which may further employ the use of one or more dedicated hardware accelerators or processing cores to perform ray or path-tracing techniques—of the server(s) 603. The encoder 616 may then encode the display data to generate encoded display data and the encoded display data may be transmitted to the client device 604 over the network(s) 606 via the communication interface 618. The client device 604 may receive the encoded display data via the communication interface 621 and the decoder 622 may decode the encoded display data to generate the display data. The client device 604 may then display the display data via the display 624.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A computer-implemented method for estimating at least one of a heart rate or breath rate of a subject, comprising:
    computing at least one spatial attention mask using an attention neural network to process an appearance map and a skin segmentation mask for at least one image in a sequence of images of the subject;
    processing the sequence of images using a motion neural network model to produce channels of feature vectors in two spatial dimensions, wherein the processing comprises applying the at least one spatial attention mask; and applying a learned channel attention mask to the channels of the feature vectors to generate at least one of an estimated heart rate or an estimated breath rate for the subject.

2. The computer-implemented method of claim 1, wherein the processing comprises applying the at least one spatial attention mask between two or more layers of the motion neural network.

3. The computer-implemented method of claim 1, wherein the attention neural network applies at least one appearance channel attention mask between two or more layers of the attention neural network to compute the at least one spatial attention mask.

4. The computer-implemented method of claim 3, wherein the at least one appearance channel attention mask is applied between a convolution layer and a pooling layer.

5. The computer-implemented method of claim 1, wherein the appearance map comprises a portion of each image of the subject that includes a face, neck, and chest region of the subject.

6. The computer-implemented method of claim 1, wherein the skin segmentation mask comprises a segmentation mask separately identifying facial skin including a forehead, cheeks, nose, neck and chest regions in each image of the subject from background, hair, eyes, eyebrows, and beard regions in each image of the subject.

7. The computer-implemented method of claim 1, wherein a frame rate at which each image in the sequence of images is received is variable and the processing comprises adjusting at least one of the estimated heart rate or the estimated breath rate based on the frame rate.

8. The computer-implemented method of claim 1, wherein one or more images in the sequence of images are compressed.

9. The computer-implemented method of claim 8, wherein the one or more images are compressed at varying levels.

10. The computer-implemented method of claim 1, further comprising determining that a ratio of the estimated heart rate and the estimated breath rate is outside of a predetermined valid range and discarding the estimated heart rate and the estimated breath rate.

11. The computer-implemented method of claim 1, wherein parameters are applied by the motion neural network model, and further comprising adjusting the parameters to reduce differences between a ground truth heart rate or breath rate and the estimated heart rate or breath rate.

12. The computer-implemented method of claim 1, wherein parameters are applied by the motion neural network model, and further comprising adjusting the parameters to reduce differences between an estimated ratio of the estimated heart rate and the estimated breath rate and ground truth ratio range.

13. The computer-implemented method of claim 1, wherein parameters are applied by the motion neural network model, and further comprising adjusting the parameters to increase correlations between the estimated heart rate and the estimated breath rate to align with expected correlations between a heart rate and a breath rate.

14. The computer-implemented method of claim 1, wherein at least one of the steps of computing, processing, and applying are performed on a server or in a data center and the sequence of images is streamed to the server or the data center from a user device.

15. The computer-implemented method of claim 1, wherein at least one of the steps of computing, processing, and applying are performed on a server or in a data center and the at least one of an estimated heart rate or an estimated breath rate is streamed to a user device.

16. The computer-implemented method of claim 1, wherein at least one of the steps of computing, processing, and applying are performed within a cloud computing environment.

17. The computer-implemented method of claim 1, wherein at least one of the steps of computing, processing, and applying are performed for training, testing, or certifying a neural network employed in a machine, robot, or autonomous vehicle.

18. The computer-implemented method of claim 1, wherein at least one of the steps of computing, processing, and applying is performed on a virtual machine comprising a portion of a graphics processing unit.

19. A system for estimating at least one of a heart rate or breath rate of a subject, comprising:
one or more processing units to implement a motion neural network model by:
    computing at least one spatial attention mask using an attention neural network to process an appearance map and a skin segmentation mask for at least one image in a sequence of images of the subject;
    processing the sequence of images using the motion neural network model to produce channels of feature vectors in two spatial dimensions, wherein the processing comprises applying the at least one spatial attention mask; and
    applying a learned channel attention mask to the channels of the feature vectors to generate at least one of an estimated heart rate or an estimated breath rate for the subject.

20. The system of claim 19, wherein the skin segmentation mask comprises a mask separately identifying regions of facial skin corresponding to at least one of: a forehead, one or more cheeks, a nose, a neck and a chest in each image of the subject from background, hair, eyes, eyebrows, and beard regions in each image of the subject.

21. A non-transitory computer-readable media storing computer instructions for estimating at least one of a heart rate or breath rate of a subject that, when executed by one or more processors, cause the one or more processors to perform the steps of:
    computing at least one spatial attention mask using an attention neural network to process an appearance map and a skin segmentation mask for at least one image in a sequence of images of the subject;
    processing the sequence of images using a motion neural network model to produce channels of feature vectors in two spatial dimensions, wherein the processing comprises applying the at least one spatial attention mask; and
    applying a learned channel attention mask to the channels of the feature vectors to generate at least one of an estimated heart rate or an estimated breath rate for the subject.

22. The non-transitory computer-readable media of claim 21, wherein the attention neural network applies at least one appearance channel attention mask between layers of the attention neural network to compute the at least one spatial attention mask.

* * * * *